(12) United States Patent
Shimizu et al.

(10) Patent No.: US 9,776,941 B2
(45) Date of Patent: Oct. 3, 2017

(54) PROCESS FOR PRODUCING ACETIC ACID

(71) Applicant: DAICEL CORPORATION, Osaka-shi, Osaka (JP)

(72) Inventors: Masahiko Shimizu, Tokyo (JP); Ryuji Saito, Otake (JP); Hiroyuki Miura, Himeji (JP)

(73) Assignee: DAICEL CORPORATION, Osaka-Shi (JP)

( * ) Notice: Subject to any disclaimer, the term of this patent is extended or adjusted under 35 U.S.C. 154(b) by 393 days.

(21) Appl. No.: 14/440,545

(22) PCT Filed: Dec. 2, 2013

(86) PCT No.: PCT/JP2013/082334
§ 371 (c)(1),
(2) Date: May 4, 2015

(87) PCT Pub. No.: WO2014/097867
PCT Pub. Date: Jun. 26, 2014

(65) Prior Publication Data
US 2015/0299084 A1    Oct. 22, 2015

(30) Foreign Application Priority Data

Dec. 21, 2012 (JP) ................. 2012-279114

(51) Int. Cl.
| | | |
|---|---|---|
| C07C 61/00 | (2006.01) | |
| C07C 51/12 | (2006.01) | |
| B01J 31/16 | (2006.01) | |
| C07C 51/44 | (2006.01) | |
| C07C 53/08 | (2006.01) | |
| B01D 3/40 | (2006.01) | |

(52) U.S. Cl.
CPC ............... *C07C 51/12* (2013.01); *B01D 3/40* (2013.01); *B01J 31/16* (2013.01); *C07C 51/44* (2013.01); *C07C 53/08* (2013.01)

(58) Field of Classification Search
CPC ......... C07C 53/08; C07C 51/12; C07C 51/44; B01D 3/40; B01J 31/16
See application file for complete search history.

(56) References Cited

U.S. PATENT DOCUMENTS

| | | |
|---|---|---|
| 5,663,430 A | 9/1997 | Morris et al. |
| 6,143,930 A | 11/2000 | Singh et al. |
| 2010/0121101 A1 | 5/2010 | Shaver |
| 2013/0116470 A1 | 5/2013 | Miura et al. |
| 2013/0303800 A1 | 11/2013 | Shimizu |

FOREIGN PATENT DOCUMENTS

| | | |
|---|---|---|
| JP | 4-266843 A | 9/1992 |
| JP | 8-67650 A | 3/1996 |
| JP | 8-245491 A | 9/1996 |
| JP | 2001-508405 A | 6/2001 |
| JP | 2012-46490 A | 3/2012 |
| JP | 2012-508166 A | 4/2012 |
| WO | WO 2010/053571 A2 | 5/2010 |
| WO | WO 2012/046593 A1 | 4/2012 |

OTHER PUBLICATIONS

International Search Report, dated in PCT/JP2013/082334, dated Mar. 4, 2014.
English translation of International Preliminary Report on Patentability and Written Opinion issued Jul. 2, 2015, in PCT International Application No. PCT/JP2013/082334.

*Primary Examiner* — Yevegeny Valenrod
*Assistant Examiner* — Blaine G Doletski
(74) *Attorney, Agent, or Firm* — Birch, Stewart, Kolasch & Birch, LLP

(57) ABSTRACT

A process for removing acetaldehyde efficiently and producing high-purity acetic acid stably is provided. Methanol is allowed to continuously react with carbon monoxide in a carbonylation reactor 1 in the presence of a catalyst system; the reaction mixture is continuously fed to a flasher 2 to form a volatile phase (2A) containing acetic acid and methyl iodide; the volatile phase (2A) is continuously fed to a splitter column 3 to form an overhead (3A) containing methyl iodide and acetaldehyde and a stream (3B) containing acetic acid; the volatile phase (2A) and/or the overhead (3A) is cooled by a first condenser C1, C3 at a predetermined cooling temperature; and the noncondensed gaseous component is further cooled by a second condenser C2, C4 to form a concentrate having a lower temperature and a higher acetaldehyde concentration. Acetaldehyde is efficiently removed by distilling the concentrate having a high acetaldehyde concentration.

17 Claims, 3 Drawing Sheets

PROCESS FOR PRODUCING ACETIC ACID

TECHNICAL FIELD

The present invention relates to a process for producing acetic acid by carbonylation of methanol, particularly relates to a process for producing acetic acid with efficiently decreased impurities (e.g., acetaldehyde) and a method for removing acetaldehyde.

BACKGROUND ART

Known industrial processes for producing acetic acid include a process which comprises allowing methanol to continuously react with carbon monoxide in a liquid phase having a low water content in the presence of a rhodium catalyst, a metal iodide, and methyl iodide to produce acetic acid with a high productivity. In the reaction liquid, there are small quantities of by-products (impurities), for example, a carbonyl compound (e.g., acetaldehyde, butylaldehyde, crotonaldehyde, 2-ethylcrotonaldehyde, and an aldol condensate thereof) and an organic iodide (e.g., a $C_{2-12}$alkyl iodide such as ethyl iodide, butyl iodide, or hexyl iodide). These impurities result in low quality of acetic acid. Extremely small quantities of reducing impurities present in acetic acid can be evaluated by a permanganate reducing substance test (permanganate time), and this evaluation method detects very small concentrations of impurities which are difficult to determine quantitatively even by a current advanced instrumental analysis. Moreover, some of these impurities have adverse effects in relation to use of acetic acid. For example, in a case where vinyl acetate is produced from ethylene and acetic acid, such impurities are known to deteriorate a palladium-series catalyst used. Unfortunately, a carbonyl compound such as acetaldehyde and a $C_{1-12}$alkyl iodide cannot be removed sufficiently by an ordinary means such as distillation, due to having boiling points in close proximity.

In a continuous reaction process, removal of a carbonyl compound in a process recycle stream has been attempted. For example, Japanese Patent Application Laid-Open Publication No. 4-266843 (JP-4-266843A, Patent Document 1) discloses a method for removing carbonyl impurities, which comprises contacting a methyl iodide stream recycled to a carbonylation reactor with an amino compound for forming a water-soluble nitrogenous derivative by a reaction with carbonyl impurities; separating an organic methyl iodide phase from an aqueous derivative phase; and distilling the methyl iodide phase to remove the carbonyl impurities. However, the carbonyl impurity content in the organic stream recycled to the carbonylation reactor is still high, and it is difficult to sufficiently remove the carbonyl impurities. Moreover, the method described in this document requires removal of the nitrogenous compound.

Japanese Patent Application Laid-Open Publication No. 8-67650 (JP-8-67650A, Patent Document 2) discloses a process for producing a highly purified acetic acid, comprising the step of allowing methanol to continuously react with carbon monoxide in the presence of a rhodium catalyst, an iodide salt, and methyl iodide to produce acetic acid, wherein the concentration of acetaldehyde in the reaction liquid is maintained at not more than 400 ppm by removing acetaldehyde from the process liquid being recycled to a reactor. This document is attentive to that the impurities are formed mostly in the reaction system and that these impurities originate in by-product acetaldehyde formed in the reaction system. Thus, according to the document, the carbonyl compound content or the organic iodide content is reduced by controlling the concentration of acetaldehyde in the reaction system, and high-purity acetic acid is obtained.

Further, this document relates to a process for producing acetic acid while removing acetaldehyde and discloses a process which comprises separating a reaction liquid into a volatile phase containing acetic acid, methyl acetate and methyl iodide and a low-volatile phase containing a rhodium catalyst; distilling the volatile phase to form a product containing acetic acid and an overhead containing methyl acetate and methyl iodide; contacting the overhead rich in carbonyl impurity (particularly acetaldehyde) with water to form an organic phase containing methyl acetate and methyl iodide and an aqueous phase containing the carbonyl impurities, and recycling the organic phase to a reactor. Moreover, as a concrete method for separating methyl iodide from the concentrate containing the carbonyl impurity, this document discloses that it is preferred to selectively extract acetaldehyde by distilling and separating an acetaldehyde stream containing methyl iodide from the process stream and subjecting the resulting acetaldehyde-rich stream to extraction with water.

According to this document, acetic acid is purified by distilling the volatile phase (by a first distillation column) to form the overhead containing methyl acetate and methyl iodide (e.g., a lower phase formed by liquid-liquid separation of the overhead); distilling the overhead by a distillation column; and subjecting an acetaldehyde-concentrated stream from the top of the column to extraction with water for removing acetaldehyde. In the whole process, although acetaldehyde is concentrated in the overhead to some degree, the concentration of acetaldehyde in the overhead is not so high. Accordingly, acetaldehyde cannot be removed efficiently in a process for treating a liquid having a low concentration of acetaldehyde.

WO2010/053571 (Patent Document 3) discloses a process for producing acetic acid, which comprises carbonylating methanol, subjecting a reaction mixture to flash distillation, distilling the resulting low boiling point component by a first distillation column to form an acetic acid stream and an exhaust gas containing a light end fraction (e.g., methyl iodide) andanaldehyde impurity (e.g., acetaldehyde), washing the exhaust gas with an absorption solvent (such as acetic acid or methanol), stripping the light end fraction and the aldehyde impurity from the absorption solvent to form a light end stream, purifying the light end stream by a second distillation column to remove the aldehyde impurity, subjecting the distillate to extraction with water to remove the aldehyde impurity, and recycling a light end fraction purified from the light end stream into the reaction system. Unfortunately, since the absolute quantity of acetaldehyde contained in the exhaust gas is small, acetaldehyde cannot be removed efficiently.

RELATED ART DOCUMENTS

Patent Documents

Patent Document 1: JP-4-266843A (Claims)
Patent Document 2: JP-8-67650A (Claims, [0007] [0018], and Examples)
Patent Document 3: WO 2010/053571 (Claims)

SUMMARY OF THE INVENTION

Problems to be Solved by the Invention

It is therefore an object of the present invention to provide a process for producing acetic acid while removing acetaldehyde efficiently.

Another object of the present invention is to provide a process for producing high-purity acetic acid while concentrating acetaldehyde by a simple manner and removing acetaldehyde efficiently from a process stream.

It is still another object of the present invention to provide a process for producing high-quality acetic acid by concentrating acetaldehyde and methyl iodide to high levels and removing acetaldehyde efficiently from the concentrate.

It is a further object of the present invention to provide a process for producing high-quality acetic acid by efficiently separating an aqueous phase (or upper phase) highly rich in acetaldehyde and an organic phase (or lower phase) containing methyl iodide and separating and removing acetaldehyde efficiently from the aqueous phase.

Means to Solve the Problems

The inventors of the present invention noted the fact that, among the components of acetic acid, methyl acetate, methyl iodide, methanol, water and acetaldehyde, acetaldehyde adversely affecting on the quality of acetic acid has a boiling point close to that of methyl iodide and has the lowest boiling point, and made intensive studies to achieve the above objects. After the studies, the inventors found that (a) methyl iodide and a large quantity of acetaldehyde are contained in a volatile phase [that is formed by flash distillation of a reaction mixture produced by carbonylation of methanol in the presence of a catalyst system containing a metal catalyst, a metal halide and methyl iodide], particularly in an overhead formed by distillation of the volatile phase; and (b) condensation of the volatile phase, particularly the overhead, by a plurality of condensers at a sequentially lower cooling temperature (condensate temperature) allows concentration of methyl iodide and acetaldehyde to high levels to separate acetaldehyde in the form of a gaseous phase or a condensate from the process stream, and the process can remove acetaldehyde efficiently compared with direct removal of acetaldehyde by simple distillation of the overhead. For example, if an overhead gas (an overhead) from a first distillation column which distills the volatile phase is cooled by a first condenser to form a condensate having a given temperature and a noncondensed gaseous component and the noncondensed gaseous component is cooled by a second condenser having a lower cooling temperature than that of the first condenser to form a condensate having a temperature lower than that of the first condensate, then acetaldehyde, which is a low boiling point component, is concentrated in the condensate of the second condenser at a higher concentration compared with the concentration of acetaldehyde in a process liquid (condensate) obtained from simple condensation of the whole amount of the overhead by only the first condenser. A process liquid mainly comprising the highly condensed acetaldehyde is subjected to acetaldehyde removing treatment (e.g., distillation) to give a concentrate having a further higher acetaldehyde concentration, and thus acetaldehyde can efficiently be removed from the system. The present invention was accomplished based on the above findings.

That is, according to the present invention, a process for producing acetic acid comprises: a reaction step for allowing methanol to continuously react with carbon monoxide in the presence of a catalyst system containing a metal catalyst (e.g., a rhodium catalyst), a metal halide (e.g., a metal iodide), and methyl iodide in a carbonylation reactor; a flash evaporation step for separating a reaction mixture, which is continuously fed from the reactor to a flasher (or an evaporator), into a volatile phase (lower boiling point component) (2A) containing produced acetic acid and methyl iodide and a less-volatile phase (or low-volatile phase, higher boiling point component) (2B) containing the metal catalyst and the metal halide; a step (or an acetic acid collection step) for separating the volatile phase (2A), which is continuously fed to at least one distillation column, into an overhead (lower boiling point component) (3A) containing methyl iodide and by-product acetaldehyde and a stream (3B) containing acetic acid; and a step for condensing a gaseous phase, containing at least methyl iodide and acetaldehyde, resulting from at least one step of these steps, to separate acetaldehyde from the condensate. In the process for producing acetic acid according to the present invention, the gaseous phase is condensed by a plurality of condensers to form condensates sequentially lower in temperature, and acetaldehyde is separated or removed from a condensate(s) enriched in acetaldehyde.

The gaseous phase containing at least acetaldehyde may be a low boiling point gaseous component resulting from at least one step of the flash evaporation step and the distillation step. For example, the gaseous phase may be a volatile phase from the flash evaporation step or may be an overhead from one or a plurality of distillation steps. The gaseous phase preferably includes at least an overhead (particularly, a first overhead having a high acetaldehyde concentration from a first distillation step). Further, the gaseous phase may be a low boiling point gaseous component contained in an offgas (waste gas) discharged or exhausted from the process. The gaseous phase may contain acetaldehyde, methyl iodide, and others.

In order to effectively separate and remove acetaldehyde from the overhead (3A), the overhead (3A) as the gaseous phase may be subjected to the plurality of condensers and cooled to form condensates and noncondensed gaseous components, wherein the condensates may have a lower temperature and a higher acetaldehyde concentration sequentially in the downstream direction (or wherein a condensate in a more downstream side has a lower temperature and a higher acetaldehyde concentration); and acetaldehyde may be separated from a condensate(s) having a high acetaldehyde concentration. Further, the volatile phase (2A) may be distilled by a first distillation column to form an overhead, and the overhead as the gaseous phase may be condensed by the plurality of condensers to separate acetaldehyde from a condensate(s) enriched in acetaldehyde.

The component to be fed to the acetaldehyde separation step is not particularly limited to the overhead (3A) or a condensate thereof, and various process streams may be used as such a component. For example, in order to effectively separate and remove acetaldehyde from the volatile phase (2A) separated by the flasher, the volatile phase (2A) as the gaseous phase may be subjected to the plurality of condensers and cooled to form condensates and noncondensed gaseous components, wherein the condensates may have a lower temperature and a higher acetaldehyde concentration sequentially in the downstream direction; and acetaldehyde may be separated from a condensate(s) having a high acetaldehyde concentration. Further, the volatile phase (2A) as the gaseous phase may be condensed by the plurality of condensers, an upper phase and/or a lower phase formed in at least one of a second and subsequent condensers [in other words, at least one of second ($2^{nd}$) to $n^{th}$ (n=2 to n) condensers except a first condenser, wherein the number of condensers is n] may be distilled by a first distillation column and/or a second distillation column to form a first overhead and/or a second overhead.

Further, the gaseous phase may be condensed by the plurality of condensers, and a condensate from at least one of a second and subsequent condensers (for example, a condensate (concentrate) enriched in acetaldehyde) may be stored in a hold tank, and acetaldehyde may be separated from the stored condensate.

Furthermore, according to the present invention, since acetaldehyde can efficiently be removed from a process stream, a useful component may be recycled to a process step. For example, the volatile phase (2A) separated in the flasher may be distilled by a first distillation column to form a first overhead, the overhead as the gaseous phase may be condensed by the plurality of condensers, and a condensate from at least one of a second and subsequent condensers (in a case where a condensate is separated into two liquid phases (or layers), an upper phase and/or a lower phase) may be distilled by a second distillation column for separating or producing a second overhead rich in acetaldehyde. In this process, the first overhead may be condensed by the plurality of condensers, a condensate from at least one of a second and subsequent condensers (in a case where a condensate is separated into two liquid phases (or layers), an upper phase and/or a lower phase) may be stored in a hold tank, and the stored liquid may be distilled by a second distillation column for separating or producing a second overhead rich in acetaldehyde. Further, the gaseous phase may be condensed by the plurality of condensers, a condensate from at least a first condenser may be stored in a decanter, a condensate from at least one of a second and subsequent condensers (for example, a condensate enriched in acetaldehyde) may be stored in a hold tank, the liquid stored in the decanter and the liquid stored in the hold tank may be combined, and acetaldehyde may be separated from the combined liquid. For example, the first overhead as the gaseous phase may be condensed by the plurality of condensers, a condensate from at least a first condenser (in a case where a condensate is separated into two liquid phases (or layers), an upper phase and/or a lower phase) may be stored in a decanter, a condensate from at least one of a second and subsequent condensers (in a case where a condensate is separated into two liquid phases (or layers) an upper phase and/or a lower phase) may be stored in a hold tank, the condensate in the decanter and the condensate in the hold tank may be combined and distilled by a second distillation column for separating or producing a second overhead rich in acetaldehyde. The liquid stored in the decanter and the liquid stored (condensate enriched in acetaldehyde) in the hold tank may be combined in a weight ratio of about 0/100 to 95/5 as the former/the latter and distilled.

The second overhead may be subjected to extraction with water to form an aqueous phase containing acetaldehyde and an organic phase containing methyl iodide, and the organic phase may be recycled to the reactor. For example, the reaction mixture may be subjected to the flasher to form a volatile phase (2A), the volatile phase (2A) may be distilled by the first distillation column to form a first overhead (3A), at least one gaseous phase selected from the volatile phase (2A) and the first overhead (3A) may be condensed by the plurality of condensers to form condensates sequentially lower in temperature, a condensate from at least one of a second and subsequent condensers (in a case where a condensate is separated into two liquid phases (or layers), an upper phase and/or a lower phase) may be distilled by a second distillation column to form a second overhead, the second overhead (if necessary, the upper phase and/or the lower phase formed in the condenser) may be subjected to extraction with water, and the resulting organic phase (heavy phase, methyl iodide phase) may be recycled to the reactor.

The gaseous phase may be condensed by 2 to 5 condensers arranged at least in series. Moreover, since acetaldehyde has a low boiling point, acetaldehyde may be separated from a condensate from at least one of a second and subsequent condensers among the plurality of condensers. For example, in a case where two condensers are used, the gaseous phase may be cooled by a first condenser to form a first condensate and a first noncondensed gaseous component, the first noncondensed gaseous component may be cooled by a second condenser of which a cooling temperature is lower than that of the first condenser to form a second condensate having a temperature lower than that of the first condensate and a second noncondensed gaseous component, and acetaldehyde may be separated from at least the second condensate.

Further, acetaldehyde may be separated and removed from a vent gas (waste gas) resulting from the process. For example, from the reaction step (reactor), a vent gas is generated at a relatively high pressure. Moreover, a vent gas is also generated from a condenser (in particular, a last condenser) for condensing the volatile phase from the flash evaporation step and from a condenser (in particular, a last condenser) for condensing the overhead from the distillation step. Thus, an offgas, containing at least methyl iodide and acetaldehyde, resulting from at least one step of the reaction step, the flash evaporation step, the storage step (condensate-holding step) and at least one distillation step may be allowed to contact with an absorption solvent, the resulting solvent may be stripped to form a gaseous phase containing at least methyl iodide and acetaldehyde, and acetaldehyde may be separated from the gaseous phase. This process may comprise a recovery (or collection) step for recovering (or collecting) a lower boiling point component with an absorption solvent.

The process may further comprise a separation and recycling step for separating acetaldehyde from at least a portion (portion or whole, or a mixture containing a portion or whole of each condensate) of acetaldehyde condensates formed in the plurality of condensers, and recycling a residual liquid from which acetaldehyde has been removed (an acetaldehyde-removed liquid) to at least one step from the reaction step to the acetaldehyde separation step. For example, the residual liquid from which acetaldehyde has been removed (e.g., a methyl iodide-rich liquid) may be recycled, e.g., to the reactor, the flasher, the splitter column, and the distillation column.

Each one of the condensates formed in the plurality of condensers has a temperature at which a mixture of volatile components is condensable, for example, a condensate formed in a first condenser may have a temperature not lower than a boiling point of acetaldehyde, and a condensate formed in at least one of a second and subsequent condensers (e.g., a last condenser) may have a temperature at which acetaldehyde is condensable (for example, a temperature lower than the boiling point). For example, the condensate formed in a first condenser among the plurality of condensers may have a temperature of not higher than 110° C. (e.g., about 20 to 110° C.) and preferably a temperature of not higher than 105° C. (e.g., about 30 to 100° C.). Moreover, the condensate formed in least one of a second and subsequent condensers (e.g., a last condenser) may have a temperature of not higher than 45° C. (e.g., about −15° C. to 45° C.) and preferably a temperature of −10° C. to 40° C. (e.g., about −5° C. to 30° C.)

Further, the present invention also includes a method for separating or removing acetaldehyde from a mixture (or liquid mixture). This method comprises: distilling a mixture containing acetic acid, methyl acetate, methyl iodide, methanol, water and acetaldehyde to form a gaseous phase containing at least methyl iodide and acetaldehyde and a liquid phase containing at least water and methanol; and condensing the gaseous phase in order to separate acetaldehyde from the condensate(s). The gaseous phase is condensed by a plurality of condensers to form condensates sequentially lower in temperature, and acetaldehyde is separated or removed from a condensate(s) enriched in acetaldehyde. According to this method, the condensate(s) enriched in acetaldehyde may be distilled to condense acetaldehyde to a higher concentration and to separate or remove the condensed acetaldehyde. For example, a condensate from at least one of a second and subsequent condensers among the plurality of condensers may be distilled for separating an overhead containing acetaldehyde (an overhead enriched in acetaldehyde). In this case, the condensate may be separated into an overhead and a liquid stream (or bottom stream) by distillation. Moreover, the gaseous phase may be condensed by a plurality of condensers, a condensate from at least a first condenser may be stored in a decanter, a condensate from at least one of a second and subsequent condensers (e.g., a last condenser) (for example, a condensate enriched in acetaldehyde) may be stored in a hold tank, the liquid stored in the decanter and the liquid stored in the hold tank may be combined and distilled to separate an overhead containing acetaldehyde. Further, in order to separate and remove acetaldehyde effectively, a condensate from at least one of a second and subsequent condensers (e.g., a last condenser) among the plurality of condensers may be distilled to form an overhead containing acetaldehyde (an overhead enriched in acetaldehyde), and the overhead may be subjected to extraction with water to form an aqueous phase containing acetaldehyde and an organic phase.

The term "a second and subsequent condensers" means, assuming that the number of condensers is n (condensers $n_1$, $n_2$, $n_3$, ... $n_n$), second, third, ..., $n^{th}$ condensers (condensers $n_2$, $n_3$, ..., $n_n$) except a first condenser (condenser $n_1$). Thus, the term "a second and subsequent condensers" may be reworded as "a second and subsequent condensers which may contain a last condenser". If the number n is 2, the term "a second and subsequent condensers" means a single condenser (i.e., a second condenser).

The term "gaseous phase" may be referred to as "gaseous phase component".

The terms "less-volatile phase" and "volatile phase" may be referred to as "less-volatile phase component" and "volatile phase component", respectively.

The term "overhead" may be referred to as "overhead component".

The term "condensate" may be referred to as "condensed component".

It is also to be understood that as used herein and in the appended claims, the singular forms "a", "an", and "the" include plural reference unless the context clearly dictates otherwise. The letter "s" following a noun designates both the plural and singular forms of that noun.

Effects of the Invention

According to the present invention, since a gaseous phase containing at least acetaldehyde is condensed by a plurality of condensers to separate and remove acetaldehyde from a condensate(s) enriched in (enriched with) acetaldehyde, acetic acid can be produced with efficiently improved acetaldehyde removal. Moreover, since the gaseous phase is condensed by the plurality of condensers to form condensates sequentially lower in temperature, acetaldehyde can be condensed and removed efficiently from a process stream by a simple manner, and thus a highly purified acetic acid can be produced. Further, condensation of the gaseous phase using the plurality of condensers results in high concentrations of acetaldehyde and methyl iodide, which have boiling points in close proximity. Thus, acetaldehyde can be removed efficiently, and high-quality acetic acid can be produced. Furthermore, condensation of the gaseous phase by a plurality of condensers efficiently forms liquid-liquid separation of an aqueous phase (or upper phase) having highly concentrated acetaldehyde and an organic phase (or lower phase) containing methyl iodide. Thus, combination of the condensates enriched with acetaldehyde (or separated condensates) formed in the plurality of condensers with the distillation and/or water extraction efficiently separates and removes acetaldehyde from the aqueous phase and produces a high-quality acetic acid with efficiently recycling methyl iodide to a reaction system.

DESCRIPTION OF EMBODIMENTS

Figure 1:
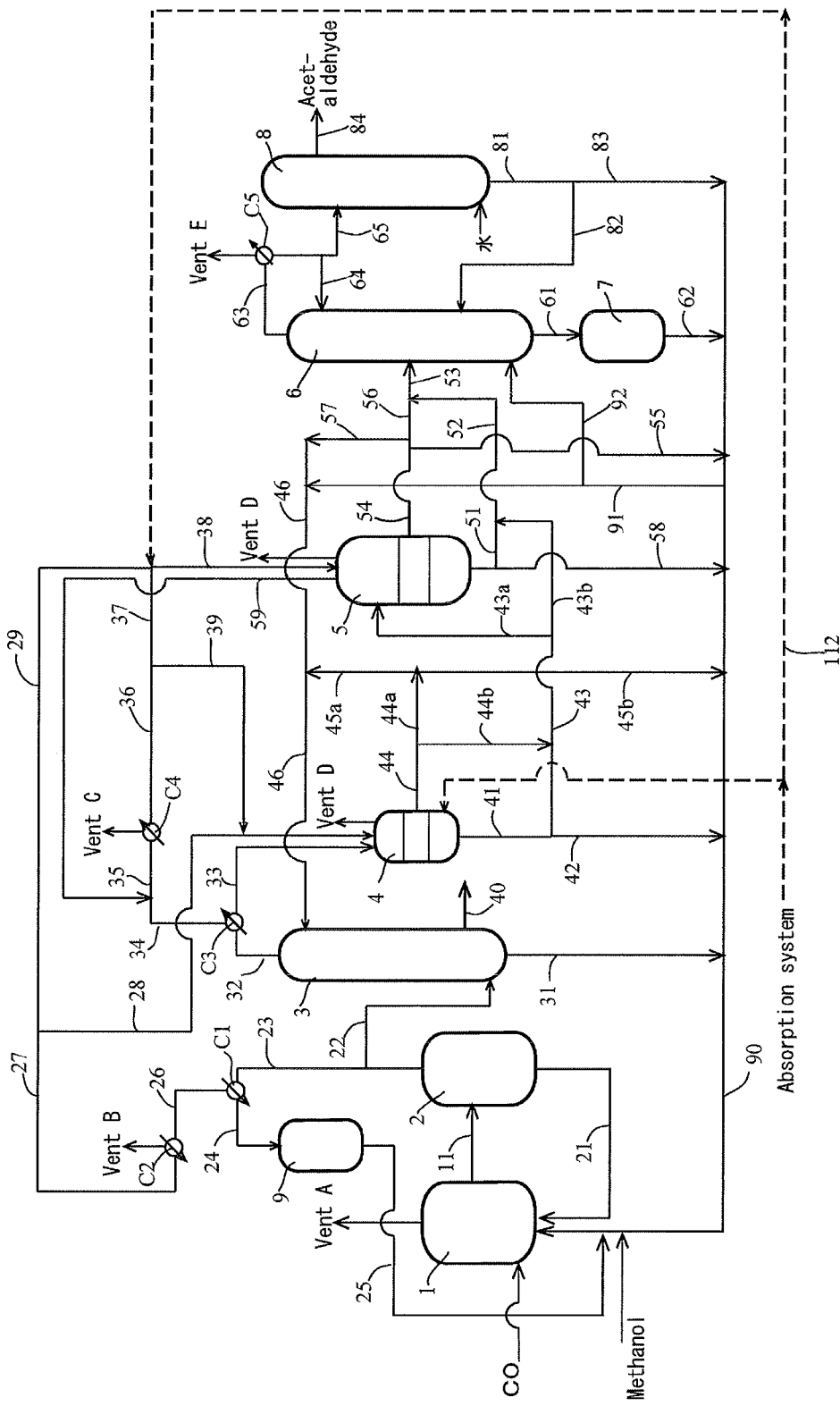
FIG. 1 is a diagram for explaining a production process (or production apparatus) of acetic acid in accordance with an embodiment of the present invention.

Hereinafter, the present invention will be explained in detail with reference to the drawings. FIG. 1 is a diagram (a flow sheet, a schematic process drawing, or a schematic plant layout drawing) for explaining a production process (or production apparatus) of acetic acid in accordance with an embodiment of the present invention.

The embodiment of FIG. 1 shows a continuous process (or apparatus) for producing acetic acid from a liquid reaction medium (or reaction mixture) produced by a continuous carbonylation reaction of methanol with carbon monoxide in the presence of a catalyst system comprising a rhodium catalyst as a metal catalyst and a co-catalyst [lithium iodide as a metal halide and methyl iodide], as well as acetic acid, methyl acetate, and a finite (or limited) amount of water.

The process (or production apparatus) comprises a reactor (reaction system) 1 for carrying out the carbonylation reaction of methanol; a flasher 2 for separating a reaction mixture (or a reaction solution) which contains product acetic acid into a volatile phase (or lower boiling point component) (2A) containing product acetic acid, methyl iodide, methyl acetate and water, and a less-volatile phase (or higher boiling point component) (2B) containing the rhodium catalyst and lithium iodide; a splitter column (distillation column) 3 for separating the volatile phase (2A) from the flasher 2 into an overhead (or first overhead, gas stream, lower-boiling point component) (3A) containing methyl iodide, methyl acetate, by-product acetaldehyde, water and others, an acetic acid stream or phase (3B) containing acetic acid as a side stream, and a liquid stream (bottom stream, higher boiling point component) (3C) containing acetic acid, water, propionic acid, and others; a decanter 4 for condensing the first overhead (3A) and temporarily holding or storing the condensate (liquid component); a buffer tank 5 for temporarily storing (or retaining) the condensate (or a lower or upper phase formed by phase-separation of the condensate in the decanter 4) from the decanter 4; a distillation column [or acetaldehyde-separating (or -removing) column] 6 for separating the condensate of the decanter 4 and/or the buffer tank 5 (or a lower or upper phase formed in the decanter 4 and/or the buffer tank 5) into a second overhead (gaseous stream, lower boiling point component) (4A) containing acetaldehyde and methyl iodide and a liquid stream (bottom stream or higher boiling point component) (4B) containing methyl iodide, methyl acetate, water, acetic acid, and others; a buffer tank 7 for temporarily storing (or retaining) the bottom stream (4B) from the distillation column 6; and an extraction column (extraction unit or extractor) 8 for subjecting the second overhead (4A) to extraction with water to form an aqueous phase (light phase) containing acetaldehyde and an organic phase (heavy phase) containing methyl iodide and to recycle the organic phase (heavy phase, raffinate) to the reactor 1. Moreover, the process (or production apparatus) shown in FIG. 1 also comprises a hold tank 9 for storing a condensate formed by cooling the volatile phase (2A) from the flasher 2 to recycle the condensate to the reactor 1; and an absorption system for absorption-treating a vent gas generated from the process.

Hereinafter, the process shown in FIG. 1 will be explained in more detail.

To the reactor 1, methanol as a liquid component and carbon monoxide as a gaseous reactant are continuously fed at predetermined flow rates. Moreover, to the reactor 1, a catalyst mixture (liquid catalyst mixture) containing a carbonylation catalyst system [a catalyst system comprising a main metal catalyst component (e.g., a rhodium catalyst) and a co-catalyst (e.g., lithium iodide and methyl iodide)] and water may be fed.

Inside the reactor 1, a carbonylation reaction of methanol proceeds with forming an equilibrium between a liquid-phase reaction system containing the reactants and the higher boiling point component such as the metal catalyst component (e.g., a rhodium catalyst and lithium iodide) and a gaseous-phase system comprising carbon monoxide, by-products (hydrogen, methane, carbon dioxide), and a vaporized lower boiling point component (e.g., methyl iodide, acetic acid as a product, and methyl acetate). In order to keep the inner pressure of the reactor 1 (e.g., reaction pressure, carbon monoxide partial pressure, and hydrogen partial pressure) constant, a vent gas (waste gas) A is withdrawn and discharged from the top of the reactor 1, and the vent gas (waste gas) A is fed to the absorption system.

Components in the reaction mixture (crude reaction solution) of the reactor 1 may include acetic acid, a lower boiling point component or impurity having a boiling point lower than that of acetic acid (e.g., methyl iodide as a co-catalyst, methyl acetate as a reaction product of acetic acid with methanol, water, and acetaldehyde as a by-product), and a higher boiling point component or impurity having a boiling point higher than that of acetic acid [e.g., a metal catalyst component (e.g., a rhodium catalyst), lithium iodide as a co-catalyst, and a $C_{3-12}$alkanecarboxylic acid such as propionic acid]. Further, various by-products derived from acetaldehyde, for example, an aldehyde compound (such as crotonaldehyde or 2-ethylcrotonaldehyde) is by-produced, and a $C_{2-12}$alkyl iodide (such as ethyl iodide, propyl iodide, butyl iodide, pentyl iodide, hexyl iodide) is also by-produced. Thus, it is preferred to separate and remove acetaldehyde, which is a main component for producing by-products from the reaction mixture and to recover (or collect) a useful component (e.g., methyl iodide) from the process stream for effective reuse.

A portion of the reaction mixture is continuously withdrawn from the reactor 1 and introduced or fed into the flasher (distillation column or catalyst separation column) 2 via a feed line 11 for flash distillation.

In the flasher (flash distillation column) 2, the reaction mixture is separated into a volatile phase (lower boiling point stream) (2A) (mainly containing acetic acid, which is a product and also plays as a reaction solvent, methyl acetate, methyl iodide, water, methanol, acetaldehyde, and others) and a less-volatile phase (higher boiling point stream) (2B) (mainly containing the metal catalyst component such as the rhodium catalyst and lithium iodide, and others), and the less-volatile phase (2B) is recycled to the reactor 1 via a bottom line 21 from the bottom of the flasher, and the volatile phase (2A) (stream mainly containing acetic acid) is continuously fed or introduced to the splitter column (or distillation column) 3 via a feed line 22 from the top or upper part of the flasher 2. Incidentally, the less-volatile phase (2B) also contains, in addition to the metal catalyst (the rhodium catalyst) and the metal halide (lithium iodide), non-evaporated components (e.g., methyl iodide, methyl acetate, water, and a trace of acetic acid). In this embodiment, the amount of the volatile phase (2A) to be separated in the flasher 2 is about 20 to 40% by volume of the whole reaction mixture.

A portion of the volatile phase (2A) is fed to a first condenser (cooling condenser, heat exchanger) C1 having a predetermined condensing temperature via a line 23 to condense and separate the volatile phase by cooling into a first condensate and a first noncondensed gaseous component having a high acetaldehyde concentration. The condensate may be separated into two liquid phases. The first condensate is fed to the hold tank 9 mentioned below. Further, the first noncondensed gaseous component is fed to a second condenser (cooling condenser, heat exchanger) C2 having a temperature lower than that of the first condenser C1 via a line 26 to separate into a second condensate having highly concentrated acetaldehyde and a second noncondensed gaseous component. The condensate may be separated into two liquid phases. Such a plurality of condensation operations can form a condensate enriched in acetaldehyde (or a condensate having a high acetaldehyde concentration). A portion of the second condensate is fed to the decanter 4 via decanter lines (a line 27 and a branch line 28), and another portion thereof is fed to the buffer tank (or hold tank) 5 via a line 29 joined to the line 27. At least a portion (portion or whole) of the second condensate is fed to an acetaldehyde-removing step [distillation column (acetaldehyde-removing column) 6]. In more detail, the second condensate is fed to the distillation column (acetaldehyde-removing column) 6 via a line and a unit (for example, the lines 27, 28, 29, the decanter 4, the buffer tank 5, and a line 52) for an acetaldehyde-removing treatment. The second noncondensed gaseous component is sent as a vent gas B to the absorption system.

In the embodiment shown in FIG. 1, the production process (or production apparatus) of acetic acid comprises a storage vessel (hold tank) 9 for storing the condensate which is formed by cooling and condensing a portion of the volatile phase (2A) from the flasher 2, and the condensate (heat-removed and condensed component) is recycled from the storage vessel 9 to the reactor 1 to control the reaction temperature. In more detail, a portion (for example, about 10 to 30% by volume) of the volatile phase (2A) is cooled (or heat-removed) and condensed in the first condenser (cooling condenser, heat exchanger) C1; the resulting condensate is stored in the hold tank 9 via a line 24; and the stored condensate is recycled to the reactor 1 via a line 25. In this manner, condensation or heat-removal of a portion of the volatile phase (2A) and recycling of the resulting condensate to the reactor facilitates temperature control of the reactor 1 in which an exothermic reaction occurs, and can reduce the loading to the splitter column (e.g., a distillation column) 3 even for a large-sized plant. In addition, since the volatile phase can be condensed to a liquid having a smaller volume, an apparatus such as the splitter column (e.g., a distillation column) 3 can be downsized (or miniaturized). Thus acetic acid can be produced with a high purity and a high yield in a resource-saving and energy-saving equipment.

In the splitter column (distillation column) 3, the volatile phase (2A) from flash distillation is separated into an overhead (overhead gas, lower boiling point stream or component) (3A) (containing at least methyl iodide and acetaldehyde, usually, methyl iodide, methyl acetate, acetaldehyde, water, methanol, acetic acid, and others) withdrawn from a top or upper part of the column via a withdrawing line 32, a side stream or acetic acid phase stream (acetic acid stream) (3B) that is recovered via a feed line 40 by side cut and mainly contains acetic acid, and a bottom liquid stream (higher boiling point stream or component) (3C) (a liquid phase containing at least water and methanol, usually, a component containing acetic acid, water, methanol, propionic acid, and others) withdrawn from a bottom or lower part of the column via a bottom line 31.

In this embodiment, the amount of the overhead (3A) separated in the splitter column 3 is about 35 to 50% by weight in the whole volatile phase (2A). Moreover, as described later, when a process liquid from the succeeding step(s) is recycled to the splitter column 3, the total amount of the volatile phase (2A) fed from the flasher 2 and the component recycled from the succeeding step(s) is subjected to distillation in the splitter column 3 to form the overhead (3A).

The acetic acid stream (3B) is fed to another distillation column (not shown) via the line 40 and then distilled for further purification. Moreover, the bottom liquid stream (higher boiling point stream or component) (3C) may be discharged via the line 31. In this embodiment, the bottom liquid stream (3C) is partly or wholly recycled to the reactor 1 via a line 90.

The overhead (3A) contains acetaldehyde and methyl iodide, in addition, acetic acid, methyl acetate, water, methanol, other impurities [e.g., an aldehyde or a carbonyl impurity (such as crotonaldehyde or butylaldehyde), a $C_{2-12}$alkyl iodide, and a $C_{3-12}$alkanecarboxylic acid] in practical cases. The overhead (3A), which is an overhead gas from the splitter column 3, is fed to the first condenser C3 via the withdrawing line 32, cooled and condensed at a predetermined temperature, and separated into a first condensate and a first noncondensed gaseous component having a high acetaldehyde concentration (or having enriched acetaldehyde). The first condensate is continuously fed to the decanter (decanter apparatus, storage vessel) 4 via a line 33 and temporarily held (stored).

Further, the first noncondensed gaseous component is fed to a second condenser C4 via lines 34, 35. In the second condenser C4, the component is cooled and condensed at a temperature lower than that of the first condenser C3 to form a second condensate enriched in acetaldehyde and a second noncondensed gaseous component, which are separated from each other.

A portion of the second condensate is fed to the decanter 4 via a decanter line (in the embodiment shown, a line 36 and a line 39 branched from the line 36 (the line 39 is joined to the line 28 in a downstream side)), and another portion thereof is fed to the buffer tank (or hold tank) 5 via a first buffer tank line (in the embodiment shown, lines 37 and 38 extending in a downstream direction from the branch point of the line 39 (a line 38 joined to the lines 29, 36, 37 in an upstream side)). The second condensate in the decanter 4 (in a case where the condensate is separated into two liquid phases (or layers), an upper phase and/or a lower phase) may be fed to the buffer tank (or hold tank) 5 via a second buffer tank line (in the embodiment shown, lines 41, 43a or lines 44, 44b, 43a).

At least a portion (whole or portion) of the second condensate is fed to the acetaldehyde-removing step [distillation column (acetaldehyde-removing column) 6]. In more detail, the second condensate is fed to the distillation column (acetaldehyde-removing column) 6 via a line and a unit (for example, the lines 39, 38, the decanter 4, the buffer tank 5, and the lines 52, 53) for an acetaldehyde-removing treatment. The second noncondensed gaseous component is sent as a vent gas (waste gas) C to the absorption system. Moreover, the noncondensed gaseous component from the decanter 4 is also sent as a vent gas (waste gas) D to the absorption system.

The volatile phase (2A) and the overhead (3A) are cooled and condensed by a plurality of cooling condensers to condense acetaldehyde efficiently. More specifically, in the production of acetic acid, the process stream (mixture), such as the volatile phase (2A), the overhead (3A), and other streams, contains various components with different boiling points, for example, acetic acid (118° C.), water (100° C.), methanol (64.1° C.), methyl acetate (57.5° C.), methyl iodide (42.5° C.), acetaldehyde (21° C.), dimethyl ether (−23.6° C.), and hydrogen iodide (−35.4° C.). The boiling point is given in the parenthesis. Among these components, hydrogen iodide and dimethyl ether, which usually exist in minor quantities, have a boiling point of not higher than 0° C., and acetaldehyde has a boiling point close to that of methyl iodide. Thus it is difficult to separate and remove only or preferentially acetaldehyde from the mixture by simple distillation. Moreover, even if the process stream (vapor mixture) is cooled by a single cooling condenser to form a condensate containing acetaldehyde, wide-ranging various components are condensed and liquefied. Thus acetaldehyde cannot be separated from the condensate efficiently.

In contrast, a plurality of condensers C1 and C2 (and/or C3 and C4), being sequentially lower in cooling temperature with more downstream direction, can condense a predetermined component depending on a cooling temperature of each condenser to separate a condensed component from a gas phase. For example, a first condensate (for example, a condensate mainly containing acetic acid, water, methanol, and others) can be separated from a first noncondensed component (for example, a gaseous component mainly containing methyl acetate, methyl iodide, acetaldehyde, and others) by a first condenser C1 or C3 set to a condensate temperature of about 25 to 100° C. Further cooling of the first noncondensed component (lower boiling point component) by a second condenser C2 or C4 set to a condensate temperature of about −10 to 50° C. can separate a second condensate containing a concentrate of a predetermined lower boiling point component (for example, a condensate mainly containing methyl acetate, methyl iodide, acetaldehyde, and others) from a second noncondensed gaseous component (e.g., a gaseous component containing traces of methyl iodide and acetaldehyde, and others).

In particular, use of a plurality of condensers can form a condensate enriched in acetaldehyde (or a condensate having a high acetaldehyde concentration). For example, in a case where two condensers, C3 and C4, are used for condensation, a first condensate formed in the first condenser C3 (in a case where a condensate is separated into two liquid phases (or layers), a whole mixture of an upper phase and a lower phase) has an acetaldehyde concentration of, e.g., 0.1 to 0.2% by weight A condensate formed in a single condenser also has the same acetaldehyde concentration. In constant, in a second condensate formed in the second condenser C4 (in a case where a condensate is separated into two liquid phases (or layers), a whole mixture of an upper phase and a lower phase), acetaldehyde can be concentrated to a concentration of 1.2 times or more (e.g., 1.5 to 3 times) as high as that of the first condensate (the above-mentioned whole mixture). For example, the second condensate may have an acetaldehyde concentration of 0.15 to 0.5% by weight.

In a case where the first condensate in the first condenser C3 is separated into two liquid phases (or layers), the upper phase may have an acetaldehyde concentration of about 500 to 5000 ppm, preferably about 1000 to 4000 ppm, and more preferably about 1200 to 3000 ppm, and the lower phase may have an acetaldehyde concentration of about 200 to 3000 ppm, preferably about 400 to 2500 ppm, and more preferably about 500 to 2000 ppm. In contrast, in a case where the second condensate in the second condenser C4 is separated into two liquid phases (or layers), the upper phase may have an acetaldehyde concentration of about 2000 to 15000 ppm and preferably about 3000 to 12000 ppm (e.g., about 5000 to 10000 ppm), and the lower phase may have an acetaldehyde concentration of about 1000 to 5000 ppm and preferably about 1500 to 4000 ppm.

In the decanter 4, the first condensate from the first condenser C3 does not necessarily need to form separated liquid phases (or layers). The first condensate usually forms an upper layer (aqueous phase) mainly containing water and acetaldehyde (and an aldehyde) and a lower layer (organic phase) mainly containing methyl iodide. Even if the first condensate is separated into two liquid phases (or layers), acetaldehyde and methyl iodide are contained in the both layers to no small extent. The volume ratio of the upper layer (or aqueous phase) relative to the lower layer (or organic phase) may for example be about 0.5/1 to 1.5/1 (e.g., about 0.7/1 to 1.3/1) as the former/the latter.

The condensate in the decanter 4 is supplied to a buffer tank line (a line 43 branched from a line 41, a line 43*a* branched from the line 43), and at least a portion of the condensate (particularly the upper phase and/or the lower phase, e.g., the lower organic phase) is fed to the buffer tank 5.

The decanter 4 for storing the first condensate from the first condenser C3 plays an important role in the process according to the present invention. Specifically, to the decanter 4, the first condensate from the first condenser C3 is fed via the feed line 33, the second condensate, having a high acetaldehyde concentration, from the second condenser C4 is fed via the line 39, and these condensates may be converged and stored in the decanter 4. Thus, control of the flow rates of the condensates to these lines 33 and 39 allows stable operation of the whole process, including the distillation column 6, and improvement of acetaldehyde-removing efficiency (removal amount of acetaldehyde).

The second condensate, having a high acetaldehyde concentration, from the second condenser C4 does not necessarily need to be fed to the decanter 4.

Moreover, the remainder of the condensate (the condensate not fed to the buffer tank 5) may be fed to the distillation column 6 via a feed line (a line 43*b* branched from the line 43). The condensate may be fed to the distillation column 6 via another route. For example, the condensate in the decanter 4 is fed to the distillation column 6 depending on the acetaldehyde concentration or the composition, if necessary, via a feed line (e.g., feed lines 44, 44*b* and/or feed lines 41, 43, 43*b*, 52) for removing acetaldehyde. Specifically, a portion of the condensate (particularly, the upper aqueous phase) may be fed to the distillation column 6 via a feed line (for example, lines 44, 44*b*).

Moreover, the condensate may be fed to the reactor 1. For example, the condensate (particularly, the lower organic phase) in the decanter 4 may be recycled to the reactor 1 by a recycle line 90 via the lines 41 and 42. Further, a portion of the condensate (particularly, the upper phase and/or the lower phase, e.g., the upper aqueous phase) may be returned to the reactor 1 by a recycle line (a recycle line 90 via the lines 44, 44*a* and a branch line 45*b* branched from the line 44*a*).

Further, the condensate may also be fed to the splitter column 3. For example, a portion of the condensate in the decanter 4 (particularly, the upper aqueous phase) may be recycled to the splitter column 3 via a recycle line (the line 44, the branch line 44*a* branched from the line 44, a branch line 45*a* branched from the line 44*a*, and a recycle line 46). A portion of the condensate (particularly, the upper aqueous phase or the lower organic phase) may be recycled to each of the splitter column 3 and the reactor 1 via these recycle lines (line 45*a* and 45*b*).

According to the embodiment of FIG. 1, the fluctuation of the stored amount (or the fluctuation of the liquid level) of the condensate in the decanter 4 is suppressed. Specifically, the fluctuation of the stored amount (or the liquid level) of the condensate in the decanter 4 is suppressed (or controlled) by recycling a portion of the condensate to the reactor 1 and/or the splitter column 3 or others via a recycle line (for example, the line (sub-line) 44*a* branched from the line 44 or the line (sub-line) 42 branched from the line 41) based on the fluctuation of the flow rate of the condensate to the decanter 4.

To the buffer tank (hold tank) 5, the condensate of the volatile phase (2A) and/or that of the overhead (3A) is fed via the line 38, and the condensate enriched in acetaldehyde is stored in the hold tank 5. Moreover, the condensate from the decanter 4 does not necessarily need to be fed to the buffer tank 5, and the condensate from the decanter 4 may usually be fed to the hold tank 5 via the line 43*a*.

The condensate in the buffer tank 5 is fed to at least the distillation column (aldehyde-removing column) 6 to form an acetaldehyde-rich second overhead. The condensate [particularly, in a case where the condensate is separated into two liquid phases (or layers), an upper phase (aqueous phase) and/or a lower phase (organic phase)] may be fed to the distillation column (aldehyde-removing column) 6 via a feed line (lines 54, 56, lines 51, 52, 53).

In a case where the condensate from the line 43*a* is temporarily stored in the buffer tank 5 and fed to the distillation column 6 via a given line, the fluctuation of the flow rate of the condensate (condensed component) can efficiently be reduced in the buffer tank 5, so that the condensate can be fed from the buffer tank 5 to distillation column 6 at a predetermined (or substantially constant) feed rate.

As described above, since the fluctuation of the flow rate of the condensate in the line 43*a* is significantly inhibited, the condensate may directly be fed to the distillation column 6. In the embodiment shown in FIG. 1, in order to further reduce the fluctuation of the flow rate, the condensate is indirectly fed to the distillation column 6 through a storage vessel (buffer tank) 5 having a buffering function. That is, the condensate from the line 43*a* is temporarily stored in the buffer tank 5 and then fed to the distillation column 6 via a given line 53. Thus, the condensate can be fed from the buffer tank 5 to the distillation column 6 via the given line 53 at a predetermined (or substantially constant) feed rate stably while efficiently suppressing the fluctuation of the flow rate of the condensate to be fed from the line 43*a* to the buffer tank 5.

The buffer tank (or hold tank) 5 for storing the second condensate from the second condenser C4 plays a significant role in the process according to the present invention. In more detail, to the feed line (lines 36, 37, 38, particularly the line 38), the following lines are joined: the line 37 for feeding the second condensate (condensate after being branched by the branch line 39) from the second condenser C4, the line 29 for feeding the second condensate of the volatile phase (2A) formed in the second condenser C2, and a line 112 for feeding the condensate of vent gases A to E. Thus, the condensate having a high acetaldehyde concentration can be stored (or held) in the buffer tank (or hold tank) 5, and distillation of the condensate in the distillation column 6 can distill off or remove acetaldehyde efficiently. Moreover, the apparatus shown in FIG. 1 is provided with the feed line 43*a* for feeding the condensate to the hold tank 5 and the feed line 43*b* for feeding the condensate to the distillation column 6, and the removal amount of acetaldehyde can be controlled by adjustment of the flow rate of the condensates in these lines to increase the removal amount of acetaldehyde.

Further, the condensate (concentrate) having a high acetaldehyde concentration stored in the hold tank 5 and the condensate stored in the decanter 4 can be joined and distilled by the distillation column 6 to increase the removal amount of acetaldehyde with the distillation column 6 operated stably, depending on the ratio of the condensate of the decanter 4 and the condensate (concentrate) of the hold tank 5. For example, the removal amount of acetaldehyde can significantly be increased by distilling the condensate (concentrate) stored in the hold tank 5. Moreover, as the ratio of the condensate from the decanter 4 relative to the condensate (concentrate) from the hold tank 5 is larger, the removal amount of acetaldehyde is reduced compared with removal of acetaldehyde from only the condensate in the hold tank 5 (but the amount is still larger than the conventional removal amount), while the total removal amount of acetaldehyde can be increased with the distillation column 6 operated stably.

Meanwhile, the condensate can also be returned to the splitter column 3 or the reactor 1. For example, the condensate in the buffer tank 5 (particularly, for example, in a case where the condensate in separated into two liquid phases (or layers), an upper phase or aqueous phase) can be recycled to the splitter column 3 via a recycle line (the line 54, the line 57 and the recycle line 46). Moreover, the condensate (for example, in a case where the condensate is separated into two liquid phases (or layers), a lower phase or organic phase) may be returned to the reactor 1 via a recycle line (the lines 58 and 90). The condensate (particularly, in a case where a condensate is separated into two liquid phases (or layers), an upper phase or aqueous phase) may be returned to the reactor 1 via a recycle line 55, which is branched from the line 54 and connected to the recycle line 90.

The offgas (vent gas) from the hold tank 5 is fed, via a line 59, to the feed line 34, which is located in an upstream side of the second condenser C4, between the first condenser C3 and the second condenser C4. The line 35 is connected from the joined portion of these lines to the second condenser C4. The line 59 may be joined to an upstream side of the first condenser C3. If necessary, the offgas may be fed as a vent gas to the absorption system.

The condensate fed to the distillation column 6 (in the embodiment shown in FIG. 1, the lower phase and/or upper phase in the decanter 4 and the lower phase and/or upper phase in the buffer tank 5) is separated into a second overhead (or lower boiling point stream or component) (4A) and a bottom stream (liquid stream, higher boiling point stream or component) (4B) in the distillation column 6; the second overhead (4A) contains acetaldehyde, a trace of methyl iodide, hydrogen iodide, dimethyl ether, carbon monoxide, hydrogen, and others, and the bottom stream (4B) contains methyl iodide, methyl acetate, water, acetic acid, and others. The second overhead (4A) is fed from a top or upper part of the column to a condenser C5 via a line 63 for cooling and condensation. A portion of the condensate is fed to the acetaldehyde extraction unit (water extraction column) 8 via a line 65, and another portion thereof is returned and refluxed to the distillation column (aldehyde-removing column) 6 via a line 64. Moreover, the noncondensed gaseous component from the condenser C5 is fed as a vent gas E to the absorption system.

The bottom stream (higher boiling point stream) (4B), which is a residual liquid (bottom fraction or column bottom fraction), is fed to the line 90 for the reactor 1 or the splitter column 3 with or without being fed to the buffer tank 7 via a line 61.

In the distillation column 6, the condensate may be distilled without passing through the decanter 4 and/or and the buffer tank 5.

In the acetaldehyde extraction unit (water extraction column) 8, the second overhead (4A) having acetaldehyde concentrated in the distillation column 6 is brought in contact with water (in the embodiment shown in FIG. 1, the second overhead (4A) is counter currently contact with water fed from a lower part of the water extraction column 8) to extract acetaldehyde with water, thereby forming an aqueous phase stream (light phase, aqueous aldehyde solution) and an organic phase (heavy phase, raffinate) containing methyl iodide. The organic phase (heavy phase, raffinate) is withdrawn from a line 81 in a bottom of the water extraction column 8, and fed to the distillation column 6 via a line 82 and/or recycled to the reactor 1 through a recycle line 90 via a line 83. In this manner, the distillation and/or recycling of the organic phase (heavy phase, raffinate) can further increase the recovery percentage of methyl iodide. Moreover, since the bottom stream (higher boiling point stream) (4B) from the distillation column 6 can also be recycled to the reactor 1 via the recycle line 90, a useful component containing methyl iodide can be used effectively. The aqueous phase stream (light phase) having a high concentration of acetaldehyde may be discharged via a line 84.

At least a portion (portion or whole) of the organic phase (heavy phase, raffinate) (4B) fed to the recycle line 90 may be recycled to the splitter column 3 via a line 91 branched from the recycle line 90. As far as stable operation of the distillation column 6 is ensured, at least a portion (portion or whole) of the organic phase (heavy phase, raffinate) (4B) fed to the line 90 or 91 may be fed to the distillation column 6 via a line 92.

The vent gas (waste gas) A from the reactor 1, the vent gas B (second gaseous component, noncondensed component) formed by cooling and condensation of the volatile phase from the flasher 2, the vent gas C (second gaseous component, noncondensed component) formed by cooling and condensation of the first overhead from the splitter column 3, the vent gas D from the decanter 4 or the hold tank 5, and the vent gas E (gaseous component, noncondensed component) formed by cooling and condensation of the second overhead from the distillation column 6 contain traces of acetaldehyde and methyl iodide, and others. The waste gas (vent gas A) from the pressurized reactor 1 has a pressure larger than those of the vent gases B to E. Thus, the vent gas (waste gas) A from the reactor 1 is fed to a high-pressure absorption column 101 via a line 105 and is treated in the absorption manner with an absorption solvent (methanol and/or acetic acid) fed from a line 104 by gas-liquid contact to form a mixture containing acetaldehyde, methyl iodide and others which are absorbed in the solvent. This mixture is withdrawn from a bottom line 107 of the high-pressure absorption column 101 and fed to a diffusion column (stripping column or stripper) 103 via a line 109.

Moreover, the vent gases B to E are joined (or converged) and fed to a low-pressure absorption column 102 via a line 106 and are treated in the absorption manner with an absorption solvent (methanol and/or acetic acid) fed from a line 104 by gas-liquid contact to form a mixture containing acetaldehyde, methyl iodide and others which are absorbed to the solvent, as described above. This mixture is withdrawn from a bottom of the low-pressure absorption column 102 via a line 108 and fed to the diffusion column (stripping column or stripper) 103 via the line 109.

In the diffusion column (stripping column or stripper) 103, a stripping treatment is carried out, and a gas stream (5A) containing acetaldehyde and methyl iodide is withdrawn from a top of the column via a line 111. The gas stream (5A) is cooled by a first condenser C6 to form (separate into) a condensate and a noncondensed gaseous component. The condensate is fed to the distillation column (acetaldehyde-removing column) 6 via a line 112. In this embodiment, the condensate is fed, through the line 112, to the distillation column (acetaldehyde-removing column) 6 via the decanter 4, the hold tank 5 and the above-mentioned line(s).

This process (or production apparatus) forms a closed-system production process for effectively recovering a useful component and effectively separating and removing an impurity component from the process stream.

Figure 3:
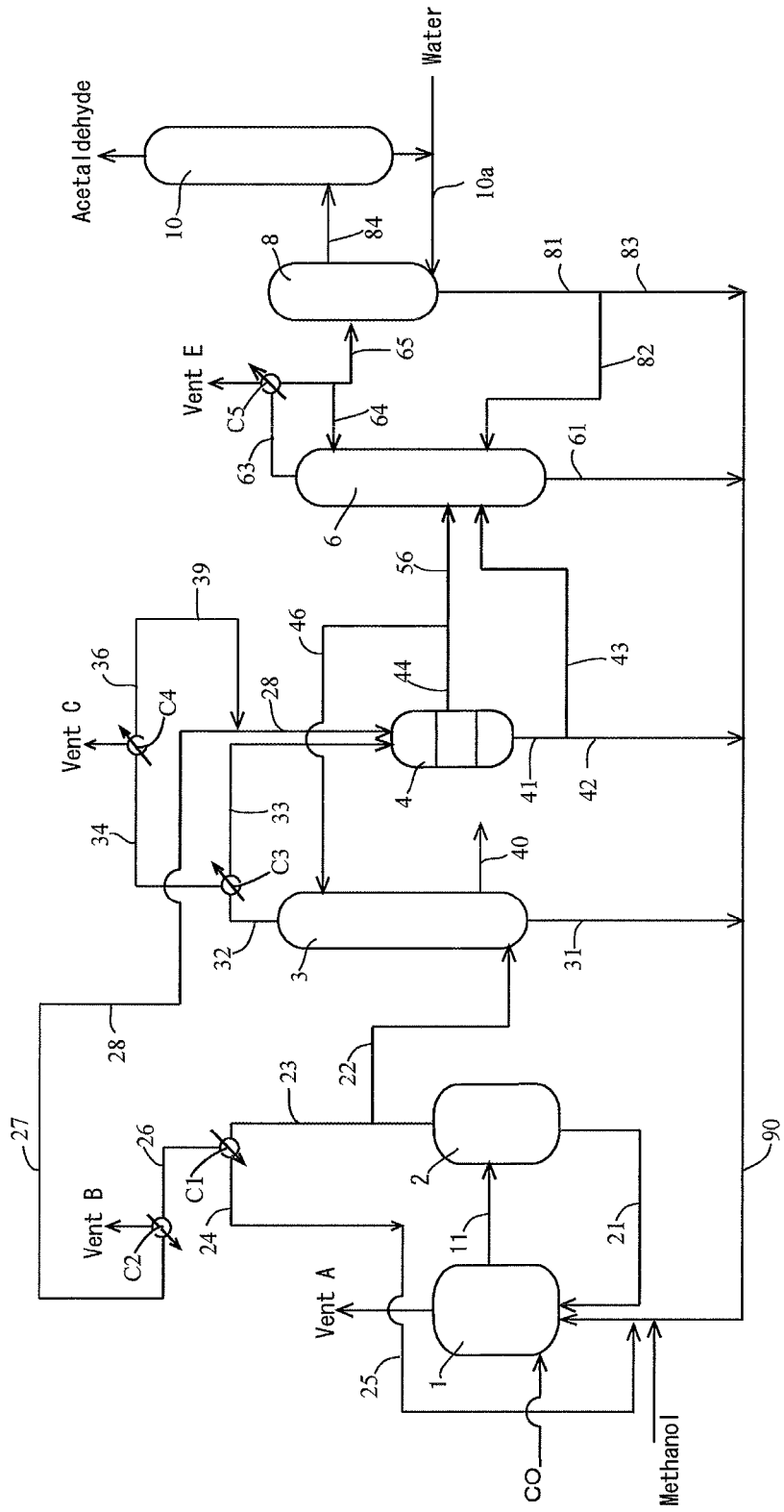
FIG. 3 is a diagram for explaining a production process (or production apparatus) of acetic acid in accordance with another embodiment of the present invention.

FIG. 3 is a diagram for explaining another embodiment of the present invention. For explanation, the same element as that in FIG. 1 is denoted by the same reference numeral as that in FIG. 1.

Figure 2:
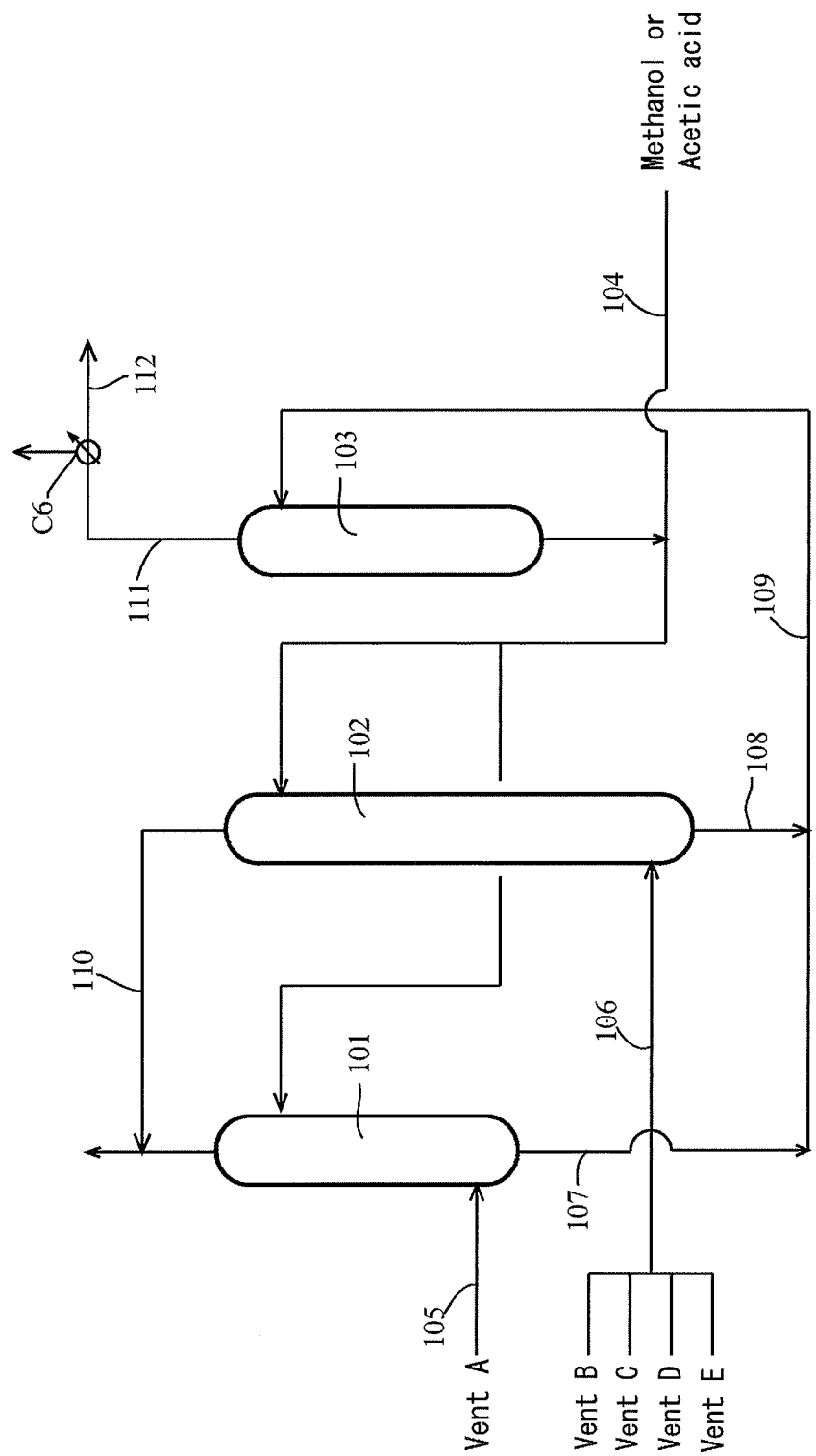
FIG. 2 is a diagram for showing an absorption system indicated in FIG. 1.

In this embodiment, the process diagram is different from that shown in FIG. 1 and FIG. 2 in that (i) the process diagram does not comprise buffer tanks 5 and 7, a hold tank 9 and an absorption system for vent gases A to E and (ii) the process diagram further provides a distillation column 10 in addition to a distillation column (acetaldehyde-removing column) 6.

Specifically, to a decanter 4, a condensate of a volatile phase (2A) from a flasher 2 (a condensate formed by sequential cooling and condensation of a volatile phase (2A) in condensers C1, C2) is fed via a branch feed line (lines 27, 28), and a condensate of a first overhead (3A) from a splitter column (distillation column) 3 (a condensate formed by sequential cooling and condensation of a first overhead (3A) in condensers C3, C4) is fed via lines 33, 39. In the decanter 4, the condensate forms two layers. At least a portion of an upper phase (aqueous phase) containing acetaldehyde can be fed to the splitter column 3 via a feed line (lines 44, 46) to form a first overhead from the column 3, and a plurality of condensers C3, C4 can further concentrate acetaldehyde. Moreover, by feeding at least a portion of the upper phase (aqueous phase) to the distillation column 6 via lines 44, 56 and subjecting the formed second overhead to extraction with water by a water extraction column 8, acetaldehyde can be removed from a light phase (aqueous stream).

Further, a portion of the lower phase (organic phase) containing methyl iodide in the decanter 4 is recycled to a reactor 1 via recycle lines (lines 42, 90), and another portion of the lower phase (organic phase) is fed to the distillation column 6. A second overhead component formed by the distillation is subjected to extraction with water by the water extraction column 8 to purify the heavy phase (raffinate) which is then recycled to the reactor 1. The upper phase and/or the lower phase in the decanter 4 may be fed to the distillation column 6.

Acetaldehyde withdrawn from an upper part or top of the water extraction column 8 is fed to the aldehyde-removing column 10. In the aldehyde-removing column 10, an acetaldehyde fraction from a top or upper part of the column and water (or aqueous stream) from a bottom or lower part of the column are separated. The separated water (or aqueous stream) is fed to the water extraction column 8 via a line 10a and used for extraction of acetaldehyde in the water extraction column 8.

Also in this process, since the condensate (concentrate) enriched in acetaldehyde from a plurality of condensers is subjected to distillation and water extraction by the distillation column 6, the water extraction column 8, and the aldehyde-removing column 10, acetaldehyde can efficiently be removed from the process stream. Moreover, since the condensate (concentrate) is also rich in methyl iodide, the recovery efficiency of methyl iodide can also be improved. Thus methyl iodide can be used effectively.

Hereinafter, each step and apparatus will be explained in detail.

[Reaction Step]

In the reaction step, it is sufficient to continuously carbonylate methanol with carbon monoxide in a reaction medium containing a carbonylation catalyst system (particularly, a rhodium catalyst and a co-catalyst containing lithium iodide and methyl iodide) and water. The reaction medium usually contains methyl acetate, acetic acid, and water.

The carbonylation catalyst system may usually comprise a metal catalyst (particularly, e.g., a cobalt catalyst, a rhodium catalyst, and an iridium catalyst), a co-catalyst, and an accelerator. The metal catalyst may be used in the form of a metal as a simple substance, a metal oxide (including a complex metal oxide), a hydroxide, an iodide, a carboxylate (e.g., an acetate), a salt of an inorganic acid (e.g., a sulfate, a nitrate, and a phosphate), a complex, and others. These metal catalysts may be used alone or in combination. The preferred metal catalyst includes a rhodium catalyst and an iridium catalyst (particularly, a rhodium catalyst).

It is preferred to use the metal catalyst in the form (the form such as a complex) dissolvable in the reaction medium (reaction liquid). As the rhodium catalyst, a rhodium iodide complex [for example, $RhI_3$, $[RhI_2(CO)_4]^-$, and [Rh $(CO)_2I_2]^-$], a rhodium carbonyl complex, or the like is preferred. The concentration of the metal catalyst is, for example, about 100 to 5000 ppm (on the basis of weight, the same applies hereinafter), preferably about 200 to 3000 ppm, more preferably about 300 to 2000 ppm, and particularly about 500 to 1500 ppm in the whole liquid phase in the reactor. The metal catalyst may be stabilized in the reaction medium by addition of an alkali metal iodide and/or water.

The co-catalyst or the accelerator may include a metal iodide, for example, an alkali metal iodide (e.g., lithium iodide, sodium iodide, and potassium iodide). The co-catalyst or the accelerator preferably includes lithium iodide. The metal iodide (for example, an alkali metal iodide) functions as a stabilizer for the carbonylation catalyst (e.g., a rhodium catalyst) under a low water content and is useful for inhibition of side reactions. These co-catalysts or accelerators may be used alone or in combination.

The concentration of the co-catalyst or accelerator is, for example, about 1 to 25% by weight, preferably about 2 to 22% by weight, and more preferably about 3 to 20% by weight in whole liquid phase in the reactor. Further, the concentration of the iodide ion in the reaction system may for example be about 0.07 to 2.5 mol/liter and preferably about 0.25 to 1.5 mol/liter.

As the accelerator contained in the catalyst system, an alkyl iodide (e.g., a $C_{1-4}$alkyl iodide such as methyl iodide, ethyl iodide, or propyl iodide), particularly methyl iodide, is utilized. Since the reaction is promoted at higher concentrations of the accelerator, the accelerator can be used at an economically advantageous concentration. The concentration of the alkyl iodide (particularly methyl iodide) is, for example, about 1 to 20% by weight, preferably about 5 to 20% by weight, and more preferably about 6 to 16% by weight (e.g., about 8 to 14% by weight) in the whole liquid phase in the reactor.

The preferred carbonylation catalyst system may comprise a rhodium catalyst and a co-catalyst containing a metal iodide (lithium iodide) and methyl iodide.

The reaction medium (or liquid phase) usually comprises product acetic acid, methyl acetate formed by a reaction of product acetic acid and raw material methanol, and water. Acetic acid also functions as a solvent. Moreover, the reaction medium (or liquid phase) usually contains unreacted raw material methanol. The proportion of methyl acetate may be about 0.1 to 30% by weight, preferably about 0.3 to 20% by weight, and more preferably about 0.5 to 10% by weight (e.g., about 0.5 to 6% by weight) in whole reaction liquid. The concentration of water in the reaction system (reaction medium) may be a low concentration. The concentration of water in the reaction system is, for example, about 0.1 to 15% by weight, preferably about 0.5 to 10% by weight, and more preferably about 0.5 to 5% by weight (e.g., about 1 to 3% by weight) and may usually be about 1 to 15% by weight (e.g., about 2 to 10% by weight) in the whole liquid phase of the reaction system. Maintaining specific concentrations of the metal iodide (e.g., an alkali metal iodide such as lithium iodide) and water in the reaction system can decrease the solubility of carbon monoxide in the liquid fed to the flasher (evaporator) and reduce the loss of carbon monoxide.

Carbon monoxide may be used as a pure gas or may be used as a gas diluted with an inactive gas (e.g., nitrogen, helium, and carbon dioxide). Moreover, exhausted gas component(s) containing carbon monoxide obtained from the succeeding step(s) may be recycled to the reaction system.

The carbon monoxide partial pressure in the reactor may for example be about 2 to 30 atmospheres and preferably about 4 to 15 atmospheres.

The carbonylation reaction generates hydrogen by a reaction of carbon monoxide with water. Hydrogen increases the catalytic activity. Thus, to the reactor 1, if necessary, hydrogen may be fed. Moreover, hydrogen may be fed to the reaction system by recycling gaseous component(s) (including hydrogen, carbon monoxide, and others) exhausted in the succeeding step(s), if necessary after purifying the gaseous component(s). The hydrogen partial pressure in the reaction system may for example be about 0.5 to 250 kPa, preferably about 1 to 200 kPa, and more preferably about 5 to 150 kPa (e.g., about 10 to 100 kPa) in terms of absolute pressure.

In the carbonylation reaction, the reaction temperature may be, for example, about 150 to 250° C., preferably about 160 to 230° C., and more preferably about 180 to 220° C. Moreover, the reaction pressure (total reactor pressure), including partial pressures of by-products, may be, for example, about 15 to 40 atmospheres.

According to the present invention, since acetaldehyde can be separated and removed efficiently, the concentration of acetaldehyde in the reactor can be reduced in spite of the continuous reaction. For example, the concentration of acetaldehyde in the reactor may be not more than 1000 ppm (e.g., 0 or detection limit to 700 ppm), preferably not more than 400 ppm (e.g., 5 to 300 ppm), and more preferably about 10 to 250 ppm in the whole liquid phase in the reactor.

In the reactor, by-products derived from acetaldehyde are also produced (for example, crotonaldehyde, which is a reducing substance, produced by aldol condensation of acetaldehyde; 2-ethylcrotonaldehyde produced by aldol condensation of hydrogenated crotonaldehyde and acetaldehyde; and hexyl iodide produced through aldol condensation of three acetaldehyde molecules, hydrogenation, and iodization). These by-products are often produced in proportion to the second to third power of the acetaldehyde concentration, and thus the reduction of acetaldehyde can efficiently suppress the formation of the by-production. According to the present invention, since the fluctuation of the acetaldehyde concentration in the reactor can also be inhibited while reducing the acetaldehyde concentration, the formation of by-products derived from acetaldehyde can significantly be inhibited.

The space time yield of the objective carboxylic acid (acetic acid) in the reaction system may be, for example, about 5 mol/Lh to 50 mol/Lh, preferably about 8 mol/Lh to 40 mol/Lh, and more preferably about 10 mol/Lh to 30 mol/Lh.

Incidentally, the reaction system is an exothermic reaction system that accompanies heat generation, and the reaction temperature may be controlled by recycling of the heat-removed condensate, installation of a heat-removable (or heat-removing) unit or a cooling unit (e.g., a jacket) for controlling the reaction temperature.

In order to remove part of the reaction heat, a vapor component (vent gas) from the reactor may be cooled with a condenser, a heat exchanger or other means and separated into a liquid component (containing acetic acid, methyl acetate, methyl iodide, acetaldehyde, water, and others) and a gaseous component (containing carbon monoxide, hydrogen, and others), and the liquid component and/or the gaseous component may be recycled to the reactor. Moreover, the vapor component (vent gas) may be withdrawn from the top of the reactor, or may be subjected to an absorption treatment to recover carbon monoxide, which may be recycled to the reactor.

[Flash Evaporation Step]

In the flash evaporation step, it is sufficient to continuously withdraw the reaction mixture from the reaction step and to separate the reaction mixture into a volatile phase (a volatile phase containing acetic acid and methyl iodide) and a non-volatile phase (a less-volatile phase containing a high boiling point catalyst component (a metal catalyst component, for example, a metal catalyst and a metal halide)). The reaction mixture may be separated into the vapor component and the liquid component with or without heating. For example, in adiabatic flash, the reaction mixture may be separated into the vapor component and the liquid component without heating and with reduced pressure, and in thermostatic flash, the reaction mixture may be separated into the vapor component and the liquid component with heating and reduced pressure. The reaction mixture may be separated into the vapor component and the liquid component by combining these flash conditions. The flash distillation may be carried out, for example, at a temperature of about 80 to 200° C. under a pressure (absolute pressure) of about 50 to 1,000 kPa (e.g., about 100 to 1,000 kPa), preferably about 100 to 500 kPa, and more preferably about 100 to 300 kPa.

The high boiling point catalyst component (metal catalyst component) may be separated from the less-volatile phase (2B) by a single or a plurality of steps. Moreover, a portion of the volatile phase (2A) may heat-removed and condensed by using a condenser or a heat exchanger and then recycled to the reactor.

[Distillation or Splitting Step (Acetic Acid Collection Step)]

The volatile phase (2A) is continuously fed to at least one splitter column (distillation column) and separated into an overhead (3A) containing methyl iodide and by-product acetaldehyde and a stream (3B) containing acetic acid to collect acetic acid. Specifically, in the distillation column, the overhead (3A) containing at least methyl iodide and acetaldehyde (usually, containing methyl iodide, methyl acetate, acetaldehyde, water, and others) is separated as a vapor from the volatile phase (2A) fed from the flasher; and the liquid stream (side cut stream, side stream) (3B) containing acetic acid is withdrawn by side cut. Incidentally, the distillation column may separate a bottom liquid stream (higher boiling point component) (3C) containing at least water and methanol (usually, acetic acid, water, methanol, propionic acid, an entrained metal catalyst component, metal halide, and others). The bottom liquid stream (3C) may be removed (discharged) from the bottom of the distillation column. Since the bottom liquid stream (3C) contains a useful component such as the metal catalyst component or acetic acid remaining without being evaporated, and the stream (3C) may be recycled to the reactor (or reaction step), the flash evaporation step (or distillation column), or others, as illustrated in the figure. Moreover, as described below, the bottom liquid stream (3C) may be recycled to the reaction system or others through a storage vessel having a buffering function.

In the splitter column (distillation column), the position of a feed port for feeding the volatile phase (2A) is not particularly limited to a specific site. For example, the position of the feed port may be in an upper, a middle, or a lower parts of the distillation column. Moreover, in the distillation column, the volatile phase (2A) may be fed at an upper position or a lower position relative to a side stream port for side-cutting the acetic acid stream. Further, the position of the side stream port for side-cutting the acetic acid stream may be in an upper, a middle, or a lower parts of the distillation column, and is usually preferably in a middle part or a lower part (or from a middle part to a lower part) of the distillation column.

As the splitter column (distillation column), there may be used a conventional distillation column, for example, a plate column, a packed column, and a flash distillation column. A distillation column such as a plate column or a packed column may be usually employed. Incidentally, the material of (or for forming) the distillation column is not limited to a specific one, and a glass, a metal, a ceramic, or others can be used. In usual, a distillation column made of a metal is used practically.

The distillation temperature and pressure in the splitter column may suitably be selected depending on the condition such as the species of the distillation column, or the removal (target) selected from the lower boiling point component and the higher boiling point component. For example, the inner temperature of the distillation column (usually, the temperature of the column top) may be controlled by adjusting the inner pressure of the column, and may be, for example, about 20 to 180° C., preferably about 50 to 150° C., and more preferably about 100 to 140° C.

Moreover, for the plate column, the theoretical number of plates is not particularly limited to a specific one, and, depending on the species of the component to be separated, is about 5 to 50, preferably about 7 to 35, and more preferably about 8 to 30. Further, in order to separate acetaldehyde highly (or with a high precision) in the distillation column, the theoretical number of plates may be about 10 to 80, preferably about 20 to 60, and more preferably about 25 to 50. Further, in the distillation operation, the reflux ratio to the distillation column may be selected from, for example, about 0.5 to 3,000, and preferably about 0.8 to 2,000 depending on the theoretical number of plates, or may be reduced by increasing the theoretical number of plates.

The overhead (3A) contains, in addition to methyl iodide and acetaldehyde, methyl acetate, water, methanol, acetic acid, an aldehyde or carbonyl impurity (such as crotonaldehyde or butyraldehyde), a $C_{2-12}$alkyl iodide, a $C_{3-12}$alkanecarboxylic acid, and others. The amount of the overhead (3A) may for example be about 5 to 70% by volume, preferably about 10 to 65% by volume, and more preferably about 12 to 60% by volume (e.g., about 15 to 50% by volume) relative to the whole volatile phase (2A).

Prior to recycling of the bottom liquid stream (3C) to the reactor (or reaction step) or the flash evaporation step (or distillation column), propionic acid may be removed off, because of deterioration of the quality of acetic acid as a final product. Moreover, usually, the acetic acid stream (crude acetic acid solution) (3B) may be further distilled (or dehydrated) in the subsequent distillation column and further introduced into an acetic acid purification column for separating a higher boiling point component (e.g., a $C_{3-12}$alkanecarboxylic acid) and a lower boiling point component from the dehydrated stream to give product acetic acid.

[Condensation and Separation Step]

According to the present invention, the gaseous phase (or gaseous phase component) containing at least acetaldehyde, particularly at least methyl iodide and acetaldehyde is cooled and condensed by a plurality of condensers to give an acetaldehyde-rich condensate, and acetaldehyde is separated and removed from the condensate. Thus, the present invention allows efficient removal of acetaldehyde even by a small-sized removal apparatus (for example, a distillation column or a water extraction unit), compared with removal of acetaldehyde by condensation of the gaseous phase once (single condensation).

The gaseous phase is practically a mixture containing acetic acid, methyl acetate, methyl iodide, methanol, water, and acetaldehyde, or a mixture containing, in addition to the above components, hydrogen iodide, dimethyl ether, the above-mentioned impurities (e.g., an aldehyde such as crotonaldehyde, an alkyl iodide such as hexyl iodide, and propionic acid). Moreover, in the embodiment described above, the volatile phase (2A), the overhead (3A) and the vent gas (5A) as the gaseous phase component are cooled and condensed to give an acetaldehyde-rich condensate, and the condensate is purified of acetaldehyde. The gaseous phase (or gaseous phase component) may be a gaseous phase generated from at least one step during the acetic acid production process, for example, a reaction step, a flash evaporation step, and at least one distillation step. As the gaseous phase, usually, a gaseous phase generated from at least one step of a flash evaporation step and a distillation step, particularly from at least a distillation step, is subjected to condensation treatment in practical cases. More specifically, the order of the high acetaldehyde content of gaseous components is as follows: (a) the first overhead (3A) from the splitter column>(b) the volatile phase (2A) from the flasher>(c) the second overhead from the distillation column and the vent gas. Thus, in order to separate and remove acetaldehyde efficiently, the gaseous phase to be condensed is practically at least one lower boiling point component of the volatile phase (2A) formed in the flash evaporation step and the first overhead (3A) formed in the first distillation column, particularly at least the first overhead (3A).

According to the present invention, the gaseous phase is condensed by cooling in sequence by a plurality of condensers which are sequentially lower in cooling temperature to form condensates, each having a low temperature, and acetaldehyde is separated from a condensate(s) enriched in acetaldehyde. The plurality of condensers is practically arranged at least in series. If necessary, each of a plurality of condensers arranged in parallel may be connected with a condenser (s) in a serial manner or serially in a downstream direction.

Further, in cooling by the condensers, a component having a boiling point higher than the temperature of the condensate is condensed and liquefied, contrarily a component having a boiling point lower than the temperature of the condensate maintains a gaseous state. Thus, cooling of the gaseous phase by a plurality of condensers with lowering the cooling temperature sequentially in the downstream direction forms condensates sequentially lower in temperature. Finally, a component to be separated and removed or to be recovered (acetaldehyde and/or methyl iodide) contained in the gaseous phase can be separated as a condensate or a gaseous component. More specifically, in a case where the gaseous phase is cooled sequentially by two condensers arranged in series, the gaseous phase is condensed in the first condenser to form a first condensate containing a condensed and liquefied higher boiling point component and a first non-condensed gaseous component containing a concentrated lower boiling point component (such as acetaldehyde), and the first gaseous component is further cooled in the second condenser to form a second condensate having a temperature lower than that of the first condensate and a higher acetaldehyde concentration and a second non-condensed gaseous component containing a component having a lower boiling point.

In the embodiment shown in the drawings, each of the volatile phase (2A) and the overhead (3A) is condensed by cooling using two condensers sequentially. If necessary, in order to further separate acetaldehyde from the second gaseous noncondensed component, the second gaseous non-condensed component may further be condensed by succeeding one or a plurality of condensers (for example, third and fourth condensers) to form a condensate enriched in acetaldehyde, and the condensate may be subjected to an acetaldehyde-removing treatment by the distillation column 6. Moreover, since a desired component can be made in a liquid form or a gaseous form depending on the cooling temperature, not only the condensed component (condensate) from the second condenser but also a condensed component (condensate) enriched in acetaldehyde formed in an appropriate condenser of the plural condensers (for example, the succeeding one or plural condensers) by cooling and condensing a gaseous component may be collected and subjected to an acetaldehyde-removing treatment by the distillation column 6. Acetaldehyde is usually condensed by the second and subsequent condensers (for example, the second, third, or fourth condenser) among the plural condensers. In particular, acetaldehyde is practically condensed and liquefied by setting the cooling temperature of at least one of the second and subsequent condensers (for example, the last condenser), particularly the last condenser, among the plural condensers, to a condensation temperature (or a temperature lower than a boiling point) of acetaldehyde.

The number of condensers is not particularly limited to a specific one. The gaseous phase is usually subjected to condensation treatment by about 2 to 5 (preferably about 2 to 3) condensers arranged in a series direction. The temperature of the condensates by plural condensers can be selected depending on the gaseous phase. The temperature of the condensate by the first condenser may be about a temperature not lower than a boiling point of acetaldehyde, for example, not higher than 110° C. (e.g., about 20 to 110° C.), preferably not higher than 105° C. (e.g., about 30 to 105° C.), and more preferably about 35 to 100° C. (e.g., about 35 to 90° C.) and may usually be about 30 to 80° C. (e.g., about 30 to 70° C.). Moreover, the temperature of the condensate(s) by the second and subsequent condensers (for example, the last condenser) in a series direction is not higher than a condensation temperature of acetaldehyde, and the temperature may be lower than a boiling point of acetaldehyde. The temperature of the condensate(s) by the second and subsequent condensers (for example, the last condenser) may for example be not higher than 50° C. (e.g., about −15° C. to 50° C.), preferably not higher than 45° C. (e.g., about −15° C. to 45° C.), more preferably not higher than 40° C. (e.g., about −10° C. to 40° C.), and particularly about −10° C. to 35° C. (e.g., about −5° C. to 30° C.) and may be about −10° C. to 25° C. (e.g., about −5° C. to 20° C.). The temperature of the condensate(s) by the second and subsequent condensers (e.g., the last condenser) may be about 0 to 40° C. (e.g., about 0 to 30° C.).

In order to condense acetaldehyde while separating acetaldehyde from other components, it is preferable that the gaseous phase be cooled by a condenser having a condensate temperature T1 of 0 to 50° C. and then the resulting gaseous phase be cooled by a condenser having a condensate temperature T2 of −15° C. to 45° C. for liquefying and condensing acetaldehyde. In particular, for liquefying acetaldehyde by condensation, the temperature different $\Delta(T1-T2)$ is preferably 1 to 60° C. (e.g., 5 to 50° C.). In order to condense methyl iodide while separating methyl iodide from other components, it is preferable that the gaseous phase be cooled by a condenser having a condensate temperature T3 of −15° C. to 50° C. and then the resulting gaseous phase be cooled by a condenser having a condensate temperature T4 of −15° C. to 45° C. for condensation of methyl iodide. The temperature difference Δ(T3−T4) is preferably about 1 to 60° C. (e.g., about 5 to 50° C.).

The condenser may include a multitubular heat exchanger, a multitubular cylindrical heat exchanger, a heat-pipe heat exchanger, an air-cooled heat exchanger, a double-pipe heat exchanger, a coil heat exchanger, a cascade heat exchanger, a plate heat exchanger, and a spiral heat exchanger.

Further, when the condensate(s) (concentrate (s)) from the second and subsequent condensers cause(s) phase separation into two liquid layers, one of an upper phase (for example, an aqueous phase containing acetaldehyde) and a lower phase (for example, an organic phase containing methyl iodide) or at least a portion (portion or whole) of both upper phase and lower phase may be subjected to an acetaldehyde-removing treatment.

In a case where the plurality of condensers is used, the gaseous noncondensed component (s) from the second and subsequent condensers (for example, the last condenser) may be fed as a vent gas to the absorption system.

The condensate formed by condensing or heat-removing a portion of the volatile phase (2A) and/or the overhead (3A) by the condenser does not necessarily need to be recycled to the reactor 1. Moreover, at least a portion (portion or whole) of the acetaldehyde concentrates (condensates) formed by the plurality of condensers may optionally be mixed together, and the (mixed) concentrates may be purified of acetaldehyde (including acetaldehyde removal or separation by distillation, water extraction, or others); and the residual liquid (or separated liquid) from which acetaldehyde has been removed may be recycled to a step from the reaction step to the acetaldehyde separation step. For example, acetaldehyde may be separated not only from the condensed component formed by the first condenser but also from the condensed component formed by the succeeding one or plural condensers (e.g., the second condenser). For example, the residual liquid (for example, a methyl iodide-rich liquid) from which acetaldehyde has been separated may for example be recycled to the reactor 1, the flasher, the splitter column 3, the distillation column 6, and others. Further, for example, when the volatile phase (2A) is not condensed by cooling, the whole amount of the volatile phase (2A) may be fed to the splitter column (distillation column) 3.

[Decanter and Buffer Tank]

Liquid-separating Unit

The decanter and the buffer tank (or hold tank) are not necessarily needed. In order to further concentrate acetaldehyde and methyl iodide by liquid-liquid separation, the apparatus according to the present invention is practically provided with at least one unit selected from the decanter and the buffer tank (or hold tank). Use of the buffer tank inhibits the fluctuation of the flow rate as described above and provides stable production of acetic acid. Moreover, when the condensate forms two layers in a buffer tank, the buffer tank functions as a decanter. Thus, both of the decanter and the buffer tank may be composed of a single decanter or buffer tank. Hereinafter, the decanter and the buffer tank will be described as a liquid-separating unit simply unless otherwise noted, and the treatment of the condensate (condensed component) will be explained.

It is sufficient that the liquid-separating unit stores a condensate of at least one gaseous phase selected from the group consisting of the volatile phase (2A) from the flash evaporation step and the overhead (3A, 4A, . . . ) from one or a plurality of distillation steps. A condensate of at least one gaseous phase selected from the group consisting of the volatile phase (2A) and the first overhead (3A), in particular a condensate of at least the first overhead (3A), is practically stored in the liquid-separating unit. Further, among the condensates of the gaseous phases (for example, at least the first overhead (3A)), the condensate from the preceding condenser (for example, at least the first condenser) and the condensate (concentrate) from at least one of the second and subsequent condensers (for example, the last condenser) may practically be stored separately (individually) in liquid-separating units. For example, the gaseous phase may be condensed by the plurality of condensers, the concentrate (condensate enriched in acetaldehyde) formed by at least one of the second and subsequent condensers (for example, the last condenser) may be stored in a hold tank, and acetaldehyde may be separated from the stored liquid. Moreover, the condensate from the preceding condenser (for example, at least the first condenser) may be stored in a decanter, and as described above, this condensate and the above-mentioned concentrate may be mixed and distilled.

The condensate of the overhead (3A), which is rich in acetaldehyde, is fed to at least the distillation column 6 from the liquid-separating unit (the decanter 4, the buffer tank 5) without passing through complicated lines, and acetaldehyde is separated and removed from the condensate.

In a case where the condensate (condensed component) causes phase separation into two liquid layers in the liquid-separating unit (the decanter 4, the buffer tank 5), the phase separation further enriches acetaldehyde in the upper phase (aqueous phase) and methyl iodide in the lower phase (organic phase). Acetaldehyde and methyl iodide are also distributed to both upper phase (aqueous phase) and lower phase (organic phase).

In order to separate and remove acetaldehyde, the upper phase and/or the lower phase, particularly the upper phase, may be distilled by at least the distillation column 6. Moreover, the upper phase and/or the lower phase, particularly the lower phase, may be recycled to at least the reactor 1. Further, the upper phase and/or the lower phase, particularly the upper phase (aqueous phase), may be distilled by the splitter column 3 and then condensed by the plurality of condensers for condensing and separating acetaldehyde.

Condensates (for example, the condensate of the first overhead (3A)) except for the condensate (highest concentrate) rich in acetaldehyde and/or methyl iodide may be fed to the liquid-separating unit for phase separation, and do not necessarily need to be fed to the liquid-separating unit. For example, in the above embodiment, the condensate in the first condenser (for example, the first condensate from the first overhead (3A)) does not necessarily need to be fed to the liquid-separating unit.

Decanter

In the embodiment shown in FIG. 1, the condensate (condensed component) is fed to a predetermined line or unit from the decanter 4 through the lower phase line 41 and the upper phase line 44. A portion of the condensate (condensed component) may be recycled through only either line (a single line) 41 or 44 to control the flow rate of the condensate to be fed to the line 43a connected to the buffer tank 5. Moreover, without reference to the separated liquid phases (the upper layer, the lower layer), the condensate may be fed or discharged to a predetermined line of unit via a single line.

The condensate in the decanter usually forms two layers. In this case, the condensate from any of the upper layer (upper phase) and/or the lower layer (lower phase) may be fed to the reactor, the splitter column, the distillation column, or others.

Either the upper layer (a portion or whole of the upper layer) or the lower layer (a portion or whole of the lower layer) may be recycled to the reaction system, or both layers may be recycled to the reaction system. The condensate to be recycled to the reaction system or others may be recycled, if necessary, after separation of acetaldehyde by a conventional manner (for example, extraction as described below).

Moreover, in a case where the condensate forms the upper layer (upper phase) and the lower layer (lower phase), the fluctuation of the liquid level (or the held amount) may totally be suppressed, or the fluctuation of the liquid phase levels (or each of the held amounts) of the both layers may be suppressed. For example, as shown in FIG. 1, the fluctuation of the liquid levels of both upper layer and lower layer can be suppressed by regulating the discharging flow rates of the upper layer and the lower layer, depending on the fluctuation of the flow rate of the condensate fed to the decanter.

Buffer Tank (Hold Tank)

The buffer tank is not necessarily needed. If necessary, through the decanter 4, the (condensate(s) of the volatile phase (2A) and/or the overhead (3A), that is, the acetaldehyde-rich condensate(s) may be supplied to the distillation column 6 for separating acetaldehyde. Moreover, the condensate in the buffer tank 5 may be subjected to the distillation column 6 or the splitter column 3, and if necessary, may be recycled to the reactor 1. The condensate (stored liquid) stored in the buffer tank 5 is rich in acetaldehyde and methyl iodide condensed by at least one of the second and subsequent condensers among the plurality of condensers. In a case where the condensate (stored liquid) causes phase separation into two liquid layers, the phase separation furthermore enriches acetaldehyde in the upper phase (aqueous phase) and methyl iodide in the lower phase (organic phase or heavy phase). Thus, for example, in a case where the condensate causes phase separation into two liquid layers in the buffer tank 5, the upper phase (aqueous phase) may be fed to the distillation column 6 and/or the reactor 1 with or without recycling to the splitter column 3, and the lower phase (organic phase) may be fed to the splitter column 3 and/or the reactor 1 with or without feeding to the distillation column 6.

The lower phase or the organic phase of the condensate in the buffer tank 5 may be fed to the distillation column 6 (aldehyde-removing column) via the feed line (the lines 51, 52, 53). The upper phase or the aqueous phase in the buffer tank 5 may be recycled to the splitter column 3 via the recycle line (the line 54, the line 57 and the recycle line 46). Further, the upper phase or the aqueous phase in the buffer tank 5 may be fed to the distillation column 6 via the feed line (the line 54, the lines 56 and 53). Distillation of the upper phase (aqueous phase) by the distillation column 6 allows efficient separation and removal of acetaldehyde as a second overhead. Moreover, distillation of the lower phase (organic phase or heavy phase) by the distillation column 6 allows efficient recovery of methyl iodide as a bottom stream.

Further, since the condensate in the buffer tank 5 contains acetaldehyde at the highest concentration, acetaldehyde can be separated from the condensate (small amount of stored liquid) by a small-sized equipment, which is industrially advantageous. Although acetaldehyde is separated from the condensate (stored liquid) in the buffer tank 5, the absolute quantity of acetaldehyde to be removed is sometimes less than the absolute quantity of by-produced acetaldehyde. Thus, in order to separate acetaldehyde, it is advantageous to merge the condensate (stored liquid) in the buffer tank 5 and a portion of the condensate stored in the decanter 4 and to separate acetaldehyde from the merged mixture. According to this manner for acetaldehyde separation, a liquid (condensate) having a higher acetaldehyde concentration compared with a conventional process can be treated to increase the removal amount of acetaldehyde even by using a conventional equipment. For example, in a case where the condensate (stored liquid) in the buffer tank 5 is distilled by the distillation column 6, if the feeding amount of the condensate to the distillation column 6 (the lines 51, 54, 53) is the same, the condensate has a higher acetaldehyde concentration compared with the conventional manner, and thus acetaldehyde can be removed in a larger quantity.

When the liquid stored in the decanter and the liquid stored in the hold tank are combined (or merged) and acetaldehyde is separated therefrom (for example, when the combined liquid is distilled by the second distillation column), the weight ratio of the liquid in the decanter relative to the liquid in the hold tank can be selected from the range of about 0/100 to 95/5 as the former/the latter and may be about 0/100 to 75/25 (e.g., about 3/97 to 90/10), preferably about 0/100 to 85/15 (e.g., about 5/95 to 80/20), more preferably about 0/100 to 75/25 (e.g., about 7/93 to 70/30) or may be about 5/95 to 50/50 or about 5/95 to 30/70.

In a case where the condensate stored in the decanter 4 and/or the hold tank 5 causes phase separation into two liquid layers, it is sufficient to separate acetaldehyde from at least one phase selected from an upper phase (aqueous phase) and a lower phase (organic phase). In a preferred embodiment, acetaldehyde is separated from an upper phase (aqueous phase) having a high acetaldehyde concentration with predominant distribution. For example, in order to increase the acetaldehyde-removing efficiency, an upper phase having a high acetaldehyde concentration of the condensate from the first condenser C3 and an upper phase having a high acetaldehyde concentration of the condensate from the second condenser C4 may be combined (or merged) and distilled by the distillation column 6.

It is useful to separate acetaldehyde from the second condensate of the first overhead (3A). With respect to a condensate, the second condensate (via lines 27, 29) of the volatile phase (2A), the second condensate (via lines 36, 37, 38) of the first overhead (3A), and the condensate (via line 112) from the offgas (vents A to E) absorption system are different from one another in acetaldehyde concentration. Each of the second condensate of the first overhead (3A) and the condensate from the offgas (vents A to E) absorption system has a relatively high acetaldehyde concentration. Thus, acetaldehyde can be separated at a high concentration by storing the whole amount of the second condensate of the volatile phase (2A) in the decanter 4 via feed lines (lines 27, 28), storing or holding the second condensate of the first overhead (3A) and the condensate from the offgas (vents A to E) absorption system in the buffer tank 5 via the feed line 38, and treating (deacetaldehyde-treating) these condensates (stored liquids), preferably at least the condensate in the buffer tank 5.

[Step for Removing Acetaldehyde and Recycling Useful Component]

In the step (separation and recycling step) for removing acetaldehyde and recycling a useful component, acetaldehyde is separated from the condensate and the residual liquid from which acetaldehyde has been removed is recycled to a step from the reaction system to the acetaldehyde separation step.

The condensate practically contains acetaldehyde, methyl iodide, acetic acid, methyl acetate, water, methanol, an aldehyde (such as crotonaldehyde or butylaldehyde), a $C_{2-12}$alkyl iodide, a $C_{3-12}$alkanecarboxylic acid, and others. In the condensate, the acetaldehyde content may be about 0.05 to 50% by weight, the methyl iodide content may be about 0.5 to 90% by weight, the methyl acetate content may be about 0 to 15% by weight, the acetic acid content may be about 0 to 80% by weight, and the water content may be about 0.1 to 40% by weight.

The method for separating acetaldehyde is not particularly limited to a specific one and can utilize a conventional method such as extraction, distillation (distillation of a process liquid containing acetaldehyde by one or a plurality of distillation columns), a combination thereof, or extractive distillation. Representatively, at least a portion (portion or whole) of the condensate (the condensates from the volatile phase (2A), the overhead (3A), and/or the vent gas (the vent gases from the reactor, the distillation column and the condenser)) is fed to the distillation column (acetaldehyde-separating column) to form the second overhead (4A) containing acetaldehyde and the residual liquid (bottom stream, bottom fraction or column bottom fraction) from which acetaldehyde has been removed. As the acetaldehyde-separating column, for example, there may be used a conventional distillation column, e.g., a plate column, a packed column, and a flash distillation column. A distillation column such as a plate column or a packed column may usually be employed.

In the above embodiment, the condensate is subjected to an acetaldehyde-removing (distillation) treatment by single distillation column. The condensate may be subjected to a plurality of acetaldehyde-removing treatments, for example, may be distilled by a plurality of distillation columns. For the removal of acetaldehyde by a distillation column, the feed liquid (the condensate to be treated) may be fed as it is, or may be fed after the feed liquid is degassed for removing gas (such as $N_2$, CO, $CO_2$). In this case, the gas may be separated after the feed liquid is heated and flashed in a separation pot, or the gas may be removed by heating the separation pot. Since overheating removes acetaldehyde together with the gas, thereby decreasing in an acetaldehyde concentration in the feed liquid, it is useful to regulate the heating temperature.

The temperature (the temperature of the column top) and the pressure (the pressure of the column top) in the acetaldehyde-separating column may be selected depending on the concentrations of acetaldehyde and methyl iodide as well as the species of the distillation column and other factors as far as at least acetaldehyde can be separated by utilizing difference between acetaldehyde and other components (particularly methyl iodide) in boiling point. For example, for a plate column, the column top pressure is about 10 to 1000 kPa, preferably about 10 to 700 kPa, and more preferably about 100 to 500 kPa in terms of absolute pressure. The inner temperature of the column (the temperature of the column top) may for example be about 10 to 80° C., preferably about 20 to 70° C., and more preferably about 40 to 60° C. The theoretical number of plates may for example be about 5 to 80, preferably about 8 to 60, and more preferably about 10 to 50.

If necessary, water is fed to the distillation column (acetaldehyde-separating column) for increasing the pressure and/or the distillation temperature in the column in order to inhibit the formation of paraldehyde and metaldehyde. Alternatively, an aldehyde condensate (e.g., paraldehyde and metaldehyde) may be positively generated by changing distillation conditions, and acetaldehyde may be separated and removed in the form of an aldehyde condensate from the distillation column. In this case, blockage or clogging of pipes due to crystallization of the aldehyde condensate may be inhibited by feeding a solvent (e.g., methanol) dissolving the aldehyde condensate to the column.

Distillation of the condensate usually separates the residual liquid (higher boiling point component (4B)) containing a useful component, methyl iodide, as a bottom stream. The residual liquid may be recycled to a step from the reaction system to the acetaldehyde separation step, for example, any of the reaction step (or reactor), the flash distillation step (or flash distillation column), the acetic acid collection step (or splitter column), and other steps. The residual liquid is practically recycled to at least the reactor.

In the above embodiment, the residual liquid may be recycled to the acetaldehyde-separating column. In the acetaldehyde-separating column, the reflux ratio can be selected from about 1 to 1000, preferably about 10 to 800, more preferably about 50 to 600 (e.g., about 100 to 600) depending on the theoretical number of plates.

[Buffer Tank]

The residual liquid (bottom stream or higher boiling point component (4B)) from the distillation column (acetaldehyde-removing column) may be recycled directly to the reaction system without by way of the buffer tank 7 or may be recycled to the reaction system through a storage vessel (such as a buffer tank) having a buffering function. Use of the storage vessel having a buffering function suppresses the flow rate fluctuation in the storage vessel and allows easy recycling of the residual liquid at a constant or substantially constant flow rate, even if the flow rate of the residual liquid fluctuates. Thus the storage vessel can reduce the adverse influence of the flow rate fluctuation on the recycling step.

Also in the storage vessel having a buffering function, as is the case with the condensation step, the flow rate may be controlled based on the degree of the flow rate fluctuation or based on a retention time of the residual liquid. In the storage vessel, the retention time of the residual liquid may for example be not less than 1 minute (e.g., about 2 minutes to 3 hours), preferably not less than 3 minutes (e.g., about 4 to 60 minutes), and more preferably not less than 12 minutes (e.g., about 15 to 40 minutes).

[Extraction Step]

The second overhead (4A) may be discharged as it is. Since the second overhead (4A) sometimes contains a useful component such as methyl iodide, methyl iodide (or a component containing methyl iodide, for example, a component containing methyl iodide, methyl acetate, and others) may be recovered from the second overhead (4A) for recycle.

The method for separating each of acetaldehyde and methyl iodide (or a component containing methyl iodide) from the second overhead (4A) may include a conventional method (for example, extraction, distillation). Representative examples of the method may include (i) a method for separating each of methyl iodide and acetaldehyde by distilling the second overhead (4A), (ii) a water extraction method for separating each of methyl iodide and acetaldehyde by subjecting the second overhead (4A) to extraction with water, based on the miscibility of acetaldehyde with water and the immiscibility of methyl iodide with water. From the viewpoint of the inhibition of the formation of an aldehyde condensate such as metaldehyde, the water extraction method (ii) is preferred. According to the water extraction method, since the proton concentration in the distillation solution is increased due to ester decomposition or others inhibits the formation of an aldehyde condensate (e.g., paraldehyde and metaldehyde), acetaldehyde can efficiently be concentrated highly and removed from the process stream.

The second overhead (4A) subjected to extraction with water forms (or be separated into) an aqueous phase (light phase or upper phase) containing acetaldehyde and an organic phase (heavy phase, methyl iodide phase or raffinate) containing methyl iodide. The water extraction may be carried out by a single extractor or a plurality of extractors. It may be possible to operate the process that the gaseous phase(s) is cooled or chilled with the plurality of condensers, the whole amount of the second and subsequent condensates (cooled liquid) (or either the upper layer or the lower layer in a case where the condenses cause phase separation into two liquid layers) may be fed to the distillation column (aldehyde-removing column), and a distillate from the distillation column may be subjected to extraction with water.

Regarding the water extraction, the extraction temperature and the extraction time are not particularly limited to specific ones. For example, the extraction may be carried out at a temperature of 0° C. to 100° C. for about 1 second to 1 hour. The extraction pressure is not particularly limited to a specific one, and an advantageous condition can be selected because of costs, and other factors. As the extractor, for example, there may be used a combination of a mixer with a settler, a combination of a static mixer with a decanter, an RDC (rotated disk contactor), a Karr column, a spray column, a packed column, a perforated plate column, a baffled column, a pulse column, and others. The extractor (extraction column) may be a single-stage extraction unit for extracting an object from a mixture of the object and water and separating the mixture into liquid phases, or may be a plurality of the single-stage extract ion units arranged in a cascade manner. For example, the extractor may be a multi-stage extraction unit that comprises a plurality of extractors (each extractor having a theoretical number of plates of 1) for sequential extraction. Moreover, the extractor may be a multi-stage extraction unit in which a plurality of extractors has been installed in a single unit, for example, a single extraction unit having the theoretical number of plates equivalent to a multi-stage extraction unit (the theoretical number of plates corresponding to multi-stage extraction). Moreover, the extraction may be either a batch system or a continuous system, or may be either a parallel extraction or a countercurrent extraction.

The organic phase may be discharged out of the system. The organic phase may be recycled to any step from the reaction system to the acetaldehyde separation step, for example, the reaction step (or reactor), the flash distillation step (or flash distillation column), the acetic acid collection step (or distillation column), or other steps. As shown in the drawings, the organic phase may be recycled to the acetaldehyde-separating column (recycled as the higher boiling point component (4B)) or may be recycled to plural steps. The organic phase (heavy phase or raffinate) is recycled to at least the reactor.

The aqueous phase (light phase or upper phase) may further be fed to the aldehyde-removing column via the line 84 and separated into an aldehyde fraction and water. The water may be used for the extraction of acetaldehyde in the water extraction column 8, or if necessary, the water may be returned to the reactor 1.

Moreover, if necessary, the gaseous phase(s) may be cooled by a plurality of condensers in a multi-stage manner, and the concentrate (or condensate) of acetaldehyde/methyl iodide may be subjected to water extraction.

[Treatment of Offgas]

The offgas (vent gas) produced from the production process of acetic acid contains at least methyl iodide and acetaldehyde. Thus, according to the present invention, at least methyl iodide and acetaldehyde may be concentrated or recovered from the offgas (vent gas) and then may be separated or used efficiently. For example, acetic acid may be produced by bringing an offgas (vent gas) produced from at least one step selected from the group consisting of the reaction step, the flash evaporation step, at least one distillation step, and at least one holding (storing) step into contact with an absorption solvent; stripping the solvent to form a gaseous phase (5A) containing at least methyl iodide and acetaldehyde; and separating and removing acetaldehyde from the gaseous phase. As the absorption solvent, at least one member selected from the group consisting of methanol and acetic acid can be used. Even if the offgas (vent gas) has a low concentration of a volatile component (for example, mainly methyl iodide, acetaldehyde, methyl acetate, water, and acetic acid, in particular, acetaldehyde and methyl iodide), such a process can concentrate the volatile component to a high concentration by stripping. Moreover, the recycling (recycling of the organic phase containing methyl iodide to the reaction system) allows effective utilization of a useful component.

As FIG. 2, an absorption treatment in the high-pressure absorption column 101 can be carried out by bringing the offgas into contact with an absorption solvent (methanol and/or acetic acid) at a high pressure (for example, 0.7 to ° 4 MPa, preferably 1 to 3.5 MPa); an absorption treatment in the low-pressure absorption column 102 can also be carried out by bringing the offgas into contact with an absorption solvent at 0 to 0.2 MPa (for example, 0.05 to 0.15 MPa). For example, the temperature of the absorption solvent may be about 0 to 40° C., the temperature of methanol may be about 0 to 40° C. (e.g., about 10 to 30° C.), and the temperature of acetic acid may be about 17 to 40° C. (e.g., about 18° C. to 30° C.). The stripping in the diffusion column (stripping column) 103 can be carried out at a pressure (e.g., about 0 to 0.2 MPa), a column top temperature (e.g., about 50 to 120° C.), and a column bottom temperature (e.g., about 90 to 170° C.). For example, the stripping of the offgas with methanol can be conducted at a column top temperature of about 40 to 70° C. and a column bottom temperature of about 90 to 110° C.; the stripping of the offgas with acetic acid can be conducted at a column top temperature of about 100 to 115° C. and a column bottom temperature of about 130 to 155° C. When methanol is used as the absorption solvent, a condensate from the condenser C6 may be refluxed in the diffusion column (stripping column) 103. Although the concentration by a condenser in the offgas treatment is not essential, the offgas such as the gaseous phase (5A) may be concentrated by a condenser if necessary, as described above.

The treatment of the offgas (vent gas) is not essential, and, for example, a vent gas from the reactor, the condenser, the distillation column, or others may be discharged. Moreover, the vent gas A from the reactor 1 may further be cooled or chilled by a heat exchanger to form a liquid component (containing acetic acid, methyl acetate, methyl iodide, acetaldehyde, water, and others) and a gaseous component (containing carbon monoxide, hydrogen, and others), and the liquid component may be recycled to the reactor 1 and the gaseous component (waste gas) may be discharged. Moreover, differently from the process shown in FIG. 1, it may be useful to treat an offgas (vent gas) produced from at least one step selected from the group consisting of the reaction step, the flash evaporation step, and at least one distillation step. For example, the offgas (vent gas) from the reaction step and that from the flash evaporation step may be treated, the offgas (vent gas) from the flash evaporation step and that from the distillation step may be treated, or the offgas (vent gas) from the plurality of distillation steps may be treated.

In the vent gas treatment, a noncondensed gaseous component which has not been liquefied by a condenser may further be separated into a condensed component and a gaseous component by a subsequent one or a plurality of condensers (e.g., second, third, and fourth condensers). The resulting liquid enriched in acetaldehyde may be treated by the acetaldehyde-removing column (acetaldehyde-removing step). In such a treatment, a gaseous component from at least one of the second and subsequent condensers (for example, the last condenser) may be fed as a vent gas to the absorption system.

EXAMPLES

The following examples are intended to describe this invention in further detail and should by no means be interpreted as defining the scope of the invention.

Comparative Example 1

According to Comparative Example 1, the overhead (3A) from the splitter column 3 was condensed by the first condenser without the second condenser, and the resulting condensate was fed to the decanter 4. That is, in the apparatus (or process) shown in FIG. 1, the first condensate (temperature: 38° C.) of the overhead (3A) from the splitter column 3 was fed to the decanter 4 to form an upper layer and a lower layer, and 75% by volume of the lower layer formed in the decanter was fed to the distillation column 6 (in line 53) through the hold tank 5 (in line 43a). The amount fed to the distillation column 6 corresponded to 37% by volume of the whole first condensate of the overhead (3A) fed to the decanter 4. Moreover, a portion of the upper layer (upper phase) was refluxed to the splitter column 3 via the line 46 without being fed to the line 43a or the line 43, and another portion thereof was recycled to the reactor 1 via the line 45b.

That is, 37% by volume of the whole first condensate of the overhead (3A) fed to decanter 4 was supplied to the distillation column 6 via the line 43a, and 63% by volume of the whole first condensate was recycled to the splitter column 3 and the reactor 1. The following were the details of the recycling: 3% by volume of the whole first condensate of the overhead (3A) fed to the decanter 4 [100% by volume from the upper layer, 0% by volume from the lower layer] and 11% by volume of the whole first condensate (the lower layer) were recycled to the reactor 1, and 47% by volume of the whole first condensate was fed to the splitter column 3 (incidentally, the remainder was a gaseous component that had not been liquefied).

The composition of the first condensate (in line 43a) fed to the hold tank 5 was as follows: 86.8% by weight methyl iodide, 11% by weight methyl acetate, 0.9% by weight acetic acid, 1.0% by weight water, 0.163% by weight acetaldehyde, and 0.001% by weight hydrogen iodide. Thereafter, the offgas from the hold tank 5 was recycled to the line 34 via the line 59 and introduced to the absorption system, in which acetaldehyde was collected, without by way of the second condenser, and then fed to the decanter 4 via the line 112. The amount of the liquid (lines 51, 52) flowing out from the hold tank 5, that is, the amount of the first condensate of the overhead (3A) fed to the distillation column 6 was 96% of the total amount (the first condensate (in line 43a)) fed to the hold tank 5, and the composition thereof was as follows: 86.8% by weight methyl iodide, 11% by weight methyl acetate, 0.8% by weight acetic acid, 0.9% by weight water, 0.138% by weight acetaldehyde, and 0.001% by weight hydrogen iodide.

Moreover, the volatile phase (lower boiling point component) (2A) from the flash evaporation step (evaporator) was supplied to two condensers (C1, C2), fed to the tank 9, and recycled to the reactor 1 without being fed to the decanter 4.

The second overhead (4A) withdrawn from the 80-plate distillation column 6 was subjected to water extraction in the extractor 8 to form methyl iodide-containing raffinate from which acetaldehyde had been extracted with water. A portion of the raffinate was recycled as it was to the 10th plate from the bottom of the distillation column 6, and another portion of the raffinate was recycled as it was to the reactor 1. The flow rate of the raffinate recycled to the distillation column 6 was held constant. The acetaldehyde extraction rate of the second overhead (4A) was 98%. Acetaldehyde (20 kg/hr) was removed by extraction-treating the whole liquid (51 kg/hr) withdrawn from the top of the 80-plate distillation column. By such a process, acetaldehyde was produced in the reactor, and 47% of the produced acetaldehyde (43 kg/hr) was removed.

After the above process was continuously operated for a predetermined time (210 hours), the concentration of acetaldehyde in the reactor was determined to be 300 ppm. The resulting product acetic acid had a permanganate time of 290 minutes. Moreover, the acetic acid had a propionic acid concentration of 81 ppm.

Example 1

According to the apparatus (or process) shown in FIG. 1, the process for producing acetic acid was conducted continuously. Specifically, the first overhead (3A) was cooled by the first condenser C3 at a controlled coolant temperature to forma first condensate having a temperature of 38° C. (and a first gaseous component having a temperature of approximately 38° C.). The first gaseous component was cooled by the second condenser C4 at a controlled coolant temperature, and a whole second condensate from the second condenser C4 was fed to the hold tank (which functioned as a decanter when the condensate forms separated liquid phases) 5 via the lines 36 and 38, where the line 36 had a temperature of 12° C., the flow rate in the line 39 was zero "0". Moreover, the first condensate was fed to the decanter 4 to form an upper layer and a lower layer. The lower layer (lower phase) was fed to the hold tank 5 via the lines 41, 43 and 43a (wherein the flow rate in the line 43b was zero "0"). Although the second condensate from the second condenser C4 and the lower layer from the decanter 4 were held in the hold tank 5, a mixture of these liquids did not form separated liquid phases. The mixture in the hold tank 5 was fed to the distillation column 6 via the lines 51, 52, 53. The conditions were the same as those of Comparative Example 1 except that the line 38 was joined not to the decanter 4 but the hold tank 5, that the amount fed to the distillation column 6 via the line 53 was the same as in the Comparative Example 1 by adjusting the flow rate of the line 43a and that of the line 38, and that the line 28 was joined not to the tank 9 but to the decanter 4.

That is, the first condensate and the second condensate of the overhead (3A) from the splitter column 3 were combined to form a mixture of these condensates, and 37% by volume of the whole condensate mixture (the condensate from the line 33 and the line 36) was fed to the line 53 (or the distillation column 6). Moreover, 13% by volume of the whole condensate mixture (the condensate from the line 33 and the line 36) [3% by volume from the upper layer, 10% by volume from the lower layer] was recycled to the reactor 1, and 47% by volume of the whole condensate was fed to the splitter column 3 (incidentally, the remainder was a gaseous component that had not been liquefied).

The composition of the first condensate (in line 43a) fed to the hold tank 5 was as follows: 86.8% by weight methyl iodide, 11% by weight methyl acetate, 0.9% by weight acetic acid, 1.0% by weight water, 0.163% by weight acetaldehyde, and 0.001% by weight hydrogen iodide. The composition of the second condensate (in line 38) was as follows: 86.1% by weight methyl iodide, 10.8% by weight methyl acetate, 0.1% by weight acetic acid, 2.4% by weight water, 0.338% by weight acetaldehyde, and 0.001% by weight hydrogen iodide. The feed ratio of the first condensate relative to the second condensate was 91.4% by weight relative to 8.6% by weight. Thereafter, the offgas from the hold tank 5 was recycled to the line 35 via the line 59. The amount (in line 51) of the mixture of the first condensate and the second condensate withdrawn from the hold tank 5, that is, the amount (in line 53) of the mixture fed to the distillation column 6, was 87% of the total amount (a total amount of the first condensate (in line 43a) and the second condensate (in line 38)) fed to the hold tank 5. Moreover, the composition of the mixture fed to the distillation column 6 was as follows: 86.9% by weight methyl iodide, 11.1% by weight methyl acetate, 0.9% by weight acetic acid, 0.8% by weight water, 0.151% by weight acetaldehyde, and 0.001% by weight hydrogen iodide.

Moreover, the second overhead (4A) from the top of the column was subjected to water extraction in the extractor 8 to form a methyl iodide-containing raffinate from which acetaldehyde had been removed. A portion of the raffinate was recycled as it was to the 10th plate of the bottom of the distillation column 6, and another portion of the raffinate was recycled as it was to the reactor 1. The flow rate of the raffinate recycled to the distillation column 6 was held constant. The acetaldehyde extraction rate of the lower boiling point component (4A) was 98%. Acetaldehyde (22 kg/hr) was removed by extraction-treating the whole liquid (51 kg/hr) withdrawn from the top of the 80-plate distillation column. By such a process, acetaldehyde was produced in the reactor, and 51% of the produced acetaldehyde (43 kg/hr) was removed.

The above process could be operated continuously and stably. After the process was continuously operated for a predetermined time (210 hours), the concentration of acetaldehyde in the reactor was determined to be 250 ppm, which revealed that the process could be operated stably while removing acetaldehyde at a high level. The resulting product acetic acid had a permanganate time of 330 minutes. Moreover, the acetic acid had a propionic acid concentration of 71 ppm.

Example 2

The experiment was carried out in the same manner as in Example 1 except that the temperature of the first condensate was 50° C.

The composition of the first condensate (in line 43a) fed to the hold tank 5 was as follows: 86.9% by weight methyl iodide, 10.9% by weight methyl acetate, 0.9% by weight acetic acid, 1.0% by weight water, 0.169% by weight acetaldehyde, and 0.001% by weight hydrogen iodide. The composition of the second condensate (in line 38) was as follows: 85.7% by weight methyl iodide, 11.6% by weight methyl acetate, 0.2% by weight acetic acid, 2.0% by weight water, 0.354% by weight acetaldehyde, and 0.001% by weight hydrogen iodide. The feed ratio of the first condensate relative to the second condensate was 84.2% by weight relative to 15.8% by weight. Thereafter, the offgas from the hold tank 5 was recycled to the line 35 via the line 59. The amount (in line 51) of the mixture of the first condensate and the second condensate withdrawn from the hold tank 5, that is, the amount (in line 53) of the mixture fed to the distillation column 6, was 80% of the total amount (a total amount of the first condensate (line 43a) and the second condensate (line 38)) fed to the hold tank 5. Moreover, the composition of the mixture fed to the distillation column 6 was as follows: 86.9% by weight methyl iodide, 11.0% by weight methyl acetate, 1.0% by weight acetic acid, 0.9% by weight water, 0.156% by weight acetaldehyde, and 0.001% by weight hydrogen iodide.

Moreover, the acetaldehyde extraction rate of the lower boiling point component (4A) was 98%. Acetaldehyde (23 kg/hr) was removed by extraction-treating the whole liquid (51 kg/hr) withdrawn from the top of the 80-plate distillation column. By such a process, acetaldehyde was produced in the reactor, and 53% of the produced acetaldehyde (43 kg/hr) was removed.

The above process could be operated continuously and stably. After the process was continuously operated for a predetermined time (250 hours), the concentration of acetaldehyde in the reactor was determined to be 230 ppm, which revealed that the process could be operated stably while removing acetaldehyde at a high level. The resulting product acetic acid had a permanganate time of 350 minutes. Moreover, the acetic acid had a propionic acid concentration of 67 ppm.

Example 3

The experiment was carried out in the same manner as in Example 1 except that the temperature of the first condensate was 63° C.

The first condensate (in line 43a) fed to the hold tank 5 was zero. The composition of the second condensate (in line 38) was as follows: 85.2% by weight methyl iodide, 12.3% by weight methyl acetate, 0.3% by weight acetic acid, 1.8% by weight water, 0.212% by weight acetaldehyde, and 0.001% by weight hydrogen iodide. The feed ratio of the first condensate relative to the second condensate was 0% by weight relative to 100% by weight. Thereafter, the offgas from the hold tank 5 was recycled to the line 35 via the line 59. The amount (in line 51) of the mixture of the first condensate and the second condensate withdrawn from the hold tank 5, that is the amount (in line 53) of the condensate fed to the distillation column 6, was 95% of the total amount (the second condensate (line 38)) fed to the hold tank 5. Moreover, the composition of the condensate fed to the distillation column 6 was as follows: 85.3% by weight methyl iodide, 12.4% by weight methyl acetate, 0.3% by weight acetic acid, 1.7% by weight water, 0.195% by weight acetaldehyde, and 0.001% by weight hydrogen iodide.

The amount fed to the distillation column 6 are just the same in Comparative Example 1 and Examples 1 to 3. In Examples 3, the liquid fed to the distillation column 6 was compensated by only the condensate (in line 38) from the second condenser C4.

Moreover, the acetaldehyde extraction rate of the lower boiling point component (4A) was 98%. Acetaldehyde (26 kg/hr) was removed by extraction-treating the whole liquid (51 kg/hr) withdrawn from the top of the 80-plate distillation column. By such a process, acetaldehyde was produced in the reactor, and 60% of the produced acetaldehyde (43 kg/hr) was removed.

The above process could be operated continuously and stably. After the process was continuously operated for a predetermined time (280 hours), the concentration of acetaldehyde in the reactor was determined to be 190 ppm, which revealed that the process could be operated stably while removing acetaldehyde at a high level. The resulting product acetic acid had a permanganate time of 400 minutes. Moreover, the acetic acid had a propionic acid concentration of 57 ppm.

INDUSTRIAL APPLICABILITY

The present invention is significantly useful as a process for stably producing high-quality acetic acid while efficiently separating and removing acetaldehyde.

DESCRIPTION OF REFERENCE NUMERALS

1 . . . Reactor
2 . . . Flasher (Evaporator)
3 . . . Splitter column (Distillation column)
4 . . . Decanter
5, 7 . . . Buffer tank
6 . . . Distillation column (Acetaldehyde-separating column)
8 . . . Extraction unit
9 . . . Hold tank

The invention claimed is:

1. A process for producing acetic acid comprising:
   a reaction step for allowing methanol to continuously react with carbon monoxide in the presence of a catalyst system containing a metal catalyst, a metal halide, and methyl iodide in a carbonylation reactor,
   a flash evaporation step for separatin a reaction mixture into a volatile phase (2A) containing produced acetic acid and methyl iodide and a less-volatile phase (2B) containing the metal catalyst and the metal halide,
   a distillation step for separating the volatile phase (2A) into an overhead (3A) containing methyl iodide and by-product acetaldehyde, and a stream (3B) containing acetic acid, and
   a condensing step for condensing a gaseous phase, containing at least acetaldehyde, resulting from at least one step selected from the group consisting of the reaction step, the flash evaporation step and the distillation step,
   wherein the gaseous phase is condensed, in the condensing step, by a plurality of condensers to form a plurality of condensates sequentially lower in temperature, and acetaldehyde is separated from at least one of the condensates, enriched in acetaldehyde.

2. A process according to claim 1, wherein the gaseous phase, containing at least methyl iodide and acetaldehyde, resulting from at least one step of the flash evaporation step and the distillation step is condensed by the plurality of condensers.

3. A process according to claim 1, wherein at least one gaseous phase selected from the group consisting of the overhead (3A) and the volatile phase (2A) is subjected to the plurality of condensers and cooled to form condensates and noncondensed gaseous components, wherein the condensates have a lower temperature and a higher acetaldehyde concentration sequentially in the downstream direction, and acetaldehyde is separated from a condensate or condensates highly enriched in acetaldehyde.

4. A process according to claim 1, wherein the gaseous phase is condensed by the plurality of condensers, and a condensate enriched in acetaldehyde from at least one of a second and subsequent condensers are stored in a hold tank, and acetaldehyde is separated from the stored condensate.

5. A process according to claim 1, wherein the gaseous phase is condensed by the plurality of condensers, a condensate from at least a first condenser is stored in a decanter, a condensate enriched in acetaldehyde from at least one of a second and subsequent condensers is stored in a hold tank, the condensate in the decanter and the condensate in the hold tank are combined and distilled for separating an overhead containing acetaldehyde.

6. A process according to claim 1, wherein the volatile phase (2A) is distilled by a first distillation column to form a first overhead, the overhead as the gaseous phase is condensed by the plurality of condensers, and
   (i) a condensate enriched in acetaldehyde from at least one of a second and subsequent condensers is distilled by a second distillation column,
   (ii) a condensate from at least one of a second and subsequent condensers is stored in a hold tank, and the stored condensate is distilled by a second distillation column, or
   (iii) a condensate from at least a first condenser is stored in a decanter, a condensate from at least one of a second and subsequent condensers is stored in a hold tank, the condensate in the decanter and the condensate in the hold tank are combined and distilled by a second distillation column,
   for separating a second overhead enriched in acetaldehyde.

7. A process according to claim 5, wherein the condensate in the decanter and the condensate in the hold tank are combined in a weight ratio of 0/100 to 95/5 as the former/the latter and distilled by a second distillation column.

8. A process according to claim 6, wherein the second overhead is subjected to extraction with water to form an aqueous phase containing acetaldehyde and an organic phase containing methyl iodide, and the organic phase is recycled to the reactor.

9. A process according to claim 1, wherein the volatile phase (2A) as the gaseous phase is condensed by the plurality of condensers, a condensate from at least one of a second and subsequent condensers is distilled by a first distillation column and/or a second distillation column to form a first overhead and/or a second overhead.

10. A process according to claim 1, wherein the gaseous phase is condensed by 2 to 5 condensers arranged in series.

11. A process according to claim 1, wherein a condensate from at least one of a second and subsequent condensers among the plurality of condensers is distilled for separating an overhead containing acetaldehyde.

12. A process according to claim 1, wherein the gaseous phase is cooled by a first condenser to form a first condensate and a first noncondensed gaseous component, the first noncondensed gaseous component is cooled by a second condenser of which a cooling temperature is lower than that of the first condenser to form a second condensate having a temperature lower than that of the first condensate and a second noncondensed gaseous component, and acetaldehyde is separated from at least the second condensate.

13. A process according to claim 1, wherein, further, an offgas (5A), containing at least methyl iodide and acetaldehyde, resulting from at least one step selected from the group consisting of the reaction step; the flash evaporation step; a storage step; and at least one distillation step, is allowed to contact with an absorption solvent, the resulting solvent is stripped to form a gaseous phase containing at least methyl iodide and acetaldehyde, and acetaldehyde is separated from the gaseous phase.

14. A process according to claim 1, wherein a condensate in a first condenser has a temperature of not higher than 110° C., and a condensate in at least one of a second and subsequent condensers has a temperature of not higher than 45° C.

15. A method for separating or removing acetaldehyde, comprising:

distilling a mixture containing acetic acid, methyl acetate, methyl iodide, methanol, water and acetaldehyde to form a gaseous phase containing at least methyl iodide and acetaldehyde and a liquid phase containing at least water and methanol, and condensing the gaseous phase to separate acetaldehyde from the gaseous phase, wherein the gaseous phase is condensed, in the condensing step, by a plurality of condensers to form a plurality of condensates sequentially lower in temperature, and acetaldehyde is separated from at least one of the condensates, enriched in acetaldehyde.

16. A method according to claim 15, wherein a condensate in a first condenser has a temperature of 20 to 110° C., and a condensate in at least one of a second and subsequent condensers has a temperature of −5° C. to 30° C.

17. A method according to claim 15, wherein a condensate from at least one of a second and subsequent condensers is distilled to form an overhead containing acetaldehyde, and the overhead is subjected to extraction with water to form an aqueous phase containing acetaldehyde and an organic phase.

* * * * *